United States Patent
Barman et al.

(10) Patent No.: US 10,328,033 B2
(45) Date of Patent: *Jun. 25, 2019

(54) METHODS AND BIOCOMPATIBLE COMPOSITIONS TO ACHIEVE SUSTAINED DRUG RELEASE IN THE EYE

(71) Applicant: Integral Biosystems LLC, Bedford, MA (US)

(72) Inventors: Shikha P. Barman, Bedford, MA (US); Moli Liu, Lowell, MA (US); Koushik Barman, Bedford, MA (US); Kevin L. Ward, Arlington, MA (US); Brendan Hackett, Somerville, MA (US)

(73) Assignee: Integral BioSystems LLC, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,065

(22) Filed: Apr. 3, 2018

(65) Prior Publication Data

US 2018/0280313 A1    Oct. 4, 2018

Related U.S. Application Data

(63) Continuation of application No. 15/509,083, filed as application No. PCT/US2015/048795 on Sep. 8, 2015, now Pat. No. 9,931,306.

(Continued)

(51) Int. Cl.
*A61F 9/00* (2006.01)
*A61K 9/00* (2006.01)
(Continued)

(52) U.S. Cl.
CPC .......... *A61K 9/7007* (2013.01); *A61F 9/0008* (2013.01); *A61K 9/0048* (2013.01);
(Continued)

(58) Field of Classification Search
None
See application file for complete search history.

(56) References Cited

U.S. PATENT DOCUMENTS 5,177,168 A    1/1993   Baron et al.
5,879,713 A    3/1999   Roth et al.
(Continued)

FOREIGN PATENT DOCUMENTS

WO    WO-2011/091205        7/2011
WO    WO-2012/114138 A1    8/2012

OTHER PUBLICATIONS

Gagandeep et al "Development and Characterization of Nano-Fiber Patch for the Treatment of Glaucoma" European Journal of Pharmaceutical Sciences vol. 53, pp. 10-16, 2014.

(Continued)

*Primary Examiner* — Aradhana Sasan
(74) *Attorney, Agent, or Firm* — Cesari and McKenna, LLP

(57) ABSTRACT

A nanostructured biocompatible wafer for drug delivery to a tissue. The wafer contains a tissue-reactive mucoadhesive polymer and a mesh formed of a plurality of polymer fibers. Also provided is a method for treating an ocular surface disease, disorder, or infection using the nanostructured biocompatible wafer. Additionally, an injectable sustained-release formulation for treating an ocular disorder is disclosed. The formulation includes a drug contained within a plurality of microparticles formed of a biodegradable polymer and are coated with a tissue-reactive compound. Further provided is a method for treating an ocular disorder by injecting the microparticulate sustained release formulation.

24 Claims, 8 Drawing Sheets

Related U.S. Application Data

(60) Provisional application No. 62/046,918, filed on Sep. 6, 2014.

(51) Int. Cl.

| | | |
|---|---|---|
| *A61K 9/16* | (2006.01) | |
| *A61K 9/70* | (2006.01) | |
| *A61K 31/56* | (2006.01) | |
| *A61K 47/10* | (2017.01) | |
| *A61K 47/32* | (2006.01) | |
| *A61K 47/34* | (2017.01) | |
| *A61P 27/02* | (2006.01) | |
| *A61P 27/04* | (2006.01) | |
| *A61P 27/06* | (2006.01) | |
| *A61K 31/573* | (2006.01) | |
| *A61K 31/5575* | (2006.01) | |

(52) U.S. Cl.
CPC .......... *A61K 9/0051* (2013.01); *A61K 9/1647* (2013.01); *A61K 31/5575* (2013.01); *A61K 31/56* (2013.01); *A61K 31/573* (2013.01); *A61K 47/10* (2013.01); *A61K 47/32* (2013.01); *A61K 47/34* (2013.01); *A61P 27/02* (2018.01); *A61P 27/04* (2018.01); *A61P 27/06* (2018.01); *A61F 9/0017* (2013.01)

(56) References Cited

U.S. PATENT DOCUMENTS

| | | | |
|---|---|---|---|
| 8,409,606 | B2 | 4/2013 | Sawhney et al. |
| 9,931,306 | B2 * | 4/2018 | Barman ................. A61K 47/10 |
| 2004/0241207 | A1 | 12/2004 | Chauhan et al. |
| 2009/0138070 | A1 | 5/2009 | Holzer et al. |
| 2009/0155326 | A1 | 6/2009 | MacK et al. |
| 2009/0269391 | A1 | 10/2009 | Bango, Jr. et al. |
| 2009/0269392 | A1 | 10/2009 | Tauber et al. |
| 2010/0104654 | A1 * | 4/2010 | Robinson ............. A61K 9/0051 424/501 |
| 2010/0331975 | A1 | 12/2010 | Nissan et al. |
| 2011/0229551 | A1 | 9/2011 | Doshi et al. |
| 2011/0268783 | A1 | 11/2011 | Shalaby et al. |
| 2012/0276186 | A1 | 11/2012 | Ghebremeskel et al. |
| 2013/0090612 | A1 | 4/2013 | De Juan et al. |
| 2014/0199364 | A1 | 7/2014 | Palasis et al. |

OTHER PUBLICATIONS

Ye et al "Chitosan-Modified, Collagen-Based Biomimetic Nanofibrous Membranes as Selective Cell Adhering Wound Dressings in the Treatment of Chemically Burned Corneas" Journal of Materials Chemistry B. vol. 2, pp. 4226-4236, 2014.

Kaur et al "Ocular Preparations: The Formulation Approach" Drug Development and Industrial Pharmacy vol. 28, pp. 473-493, 2002.

Yuan et al "Ocular Drug Delivery Nanowafer with Enhanced Therapeutic Efficacy" ACS Nano vol. 9, pp. 1749-1758, 2015.

* cited by examiner

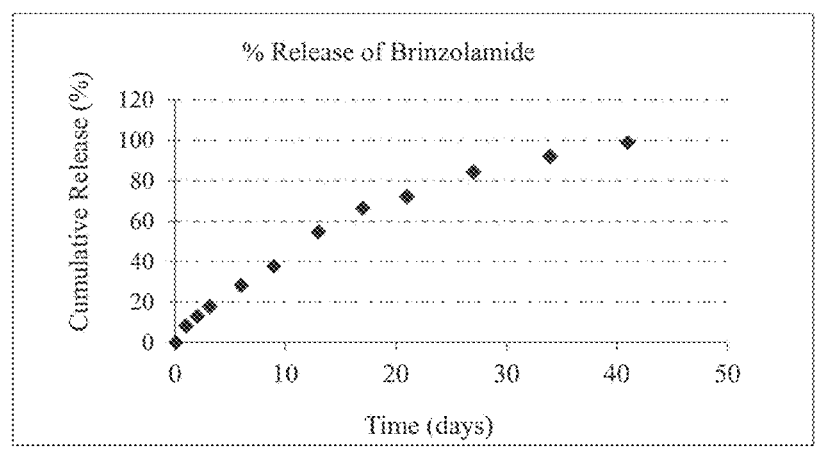
FIG. 4D
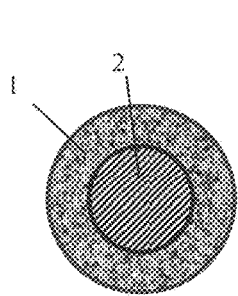 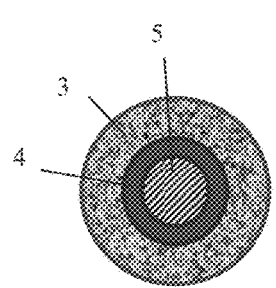 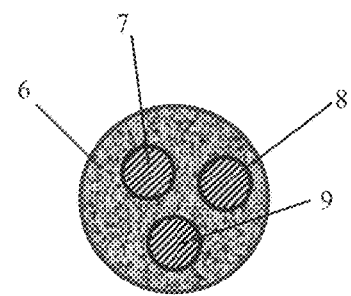
FIG. 5A  FIG. 5B  FIG. 5C

METHODS AND BIOCOMPATIBLE COMPOSITIONS TO ACHIEVE SUSTAINED DRUG RELEASE IN THE EYE

CROSS-REFERENCE TO RELATED APPLICATIONS

The present application is a continuation of U.S. patent application Ser. No. 15/509,083, filed on Mar. 6, 2017, which is the National Stage of International Application No. PCT/US2015/048795, filed on Sep. 8, 2015, which claims priority to U.S. Provisional Application No. 62/046,918, filed on Sep. 6, 2014. The content of these three applications is hereby incorporated by reference in its entirety.

BACKGROUND

Field

This application relates to methods and compositions for administering pharmaceutical compositions to the ocular surface, the anterior chamber, and the posterior chamber of the eye for treating ocular diseases and disorders.
Background Information
Limitations of Current Therapies for the Eye Currently, most ophthalmic drugs are administered in the form of eye-drops. With a single eye-drop, only about 5% of the drug administered is absorbed by ocular tissue; the rest is lost through naso-lacrimal drainage. Additionally, fast drainage of eye-drop formulations from the ocular space makes frequent administration regimens necessary. This leads to patient's incompliance due to inconvenience, leading to a lower therapeutic value of the treatment.

Most ophthalmic drugs are hydrophobic small molecules. For this reason, liquid eye-drops are typically suspensions due to the limited solubility of ophthalmic drugs in water. For drug suspensions to be bioavailable, the drug must be solubilized first in the eye prior to absorption. The fast clearance rate of fluid from the eye results in low drug absorption rates and inefficient delivery.

On the other hand, fully solubilized drug eye-drop solutions lead to spikes in drug concentration levels followed by fast clearance. This leads to possibly irritating high levels of drug followed by less than therapeutic levels of the drug.

Most commercial formulations of prostaglandins for glaucoma treatment contain a commonly used preservative, benzalkonium chloride, which has been correlated with ocular toxicity in both in-vivo and in-vitro studies, including corneal neurotoxicity. Chronic use of a preservative has been correlated with apoptosis of conjunctival cells and induction of inflammation. Thus, preservative-free strategies for glaucoma treatments should be part of the design space for future therapeutic regimens.

Historically, sustained-release delivery systems were designed to provide continuous release of a therapeutic agent to avoid the peak and trough therapeutic agent levels that occur in the aqueous humor with topical dosing. Sustained release delivery systems for front-of-the-eye ocular delivery include, e.g., viscous solutions to enhance residence time, punctal plugs, and drug-coated contact lenses. All of these systems have advantages over eye-drops and distinct disadvantages. For example, in addition to manufacturing challenges, drug-eluting contact lenses impact the vision field with inherent alterations in the visual acuity of the lens as the drug depletes, and punctal plugs require installation by a clinician.

Turning to therapy for diseases in the posterior chamber of the eye, drugs are typically injected in the vitreous, sub-tenon's, or suprachoroidal tissue space. Multiple injections into the back of the eye can increase the risk of infections and retinal detachment. Thus, sustained release systems have become the answer to the treatment of chronic ocular disorders, obviating the need for frequent injections.

Biodegradable implants and poly(lactic-co-glycolic acid) (PLGA) microspheres have been most commonly used for sustained release drug delivery. In the case of microspheres, the manufacturing process generates microspheres which have a size distribution. Depending upon the process, the size distribution of the delivery system can vary widely, resulting in wide variations in drug release. Wide size distributions can result in a release rate that is not precise or predictable, since the rate of diffusion of a drug through a matrix is dependent upon its path length. Other factors affecting release rate are polymer composition, rate of hydration of the microsphere matrix, and erosion of the matrix due to biodegradation. Thus, matrices with smaller sizes have shorter diffusion path-lengths and faster degradation rates, leading to faster drug release.

It is difficult to achieve a constant rate of drug release per unit time for PLGA microspheres prepared by standard techniques. Typically, what is observed is a "burst" of drug followed by a "trickling" of drug from the matrices, until the matrix disintegrates completely, leading to sudden, unpredictable, and complete release of encapsulated drug, i.e., dose dumping. Dose dumping can lead to undesirable and unanticipated side effects due to drug toxicity. Tighter control of microsphere size has been accomplished by sieving methods, although this often leads to significant losses of encapsulated drug due to the difficulty of sieving to narrow particle size ranges.

Additionally, microspheres tend to aggregate into a mass when injected into a tissue, also leading to unpredictable drug release rates. This is a major issue, since the aggregated microspheres behave like a much larger delivery system, having drug release rates dependent on the dimensions and characteristics of the aggregations. Since the shape and internal characteristic of the aggregates is unpredictable and can vary with each injection, the rate of release of the drug will vary with each administration. This leads to variability and unpredictability of drug pharmacokinetics.

As mentioned above, if drug levels are too low, the drug is ineffective and if the drug levels are too high, toxicity can result. Thus, in addition to precise and predictable drug release, a critical need exists to keep the dosage form of microspheres in a dispersed state after in-vivo administration in order to ensure consistency in drug bioavailability.
Related Art U.S. Pat. No. 8,409,606 describes a medical prosthesis for blocking or reducing tear flow through a tear duct of a human eye while delivering a drug to the eye. The prosthesis contains a dehydrated, cross-linked synthetic hydrophilic polymer containing a therapeutic agent. The prosthesis is sized to be readily inserted into the patient's tear duct and quickly swells upon insertion to at least 1 mm in cross-sectional width to conformably fit the canaliculus into which it is inserted. The prosthesis requires a specialized instrument to allow a doctor to insert it into the eye of the patient.

U.S. Patent Application Publication 2013/0090612 describes devices which are designed to rest on the surface of the eye out of the field of vision but surrounding the cornea along at least a portion of conjunctival sac of the upper and lower lids of the eye. The devices have reservoirs containing eye medications. Some of the devices described in the application are completely non-bioerodible and others partially bioerodible.

International Patent Application Publication WO/2011/091205 describes intracameral implants including at least one therapeutic agent for treatment of an ocular condition. The implants are not anchored to the ocular tissue, but rather are held in place by currents and gravity present in the anterior chamber of an eye. The polymeric, biodegradable implants described provide sustained release of at least one therapeutic agent to both the trabecular meshwork and associated ocular tissue and the fluids within the anterior chamber of an eye. The intracameral implants must be injected by a clinician and cannot be removed if unanticipated adverse effects occur without additional surgical intervention.

U.S. Patent Application Publication 2012/0276186 describes a sustained release, biodegradable polyethylene glycol (PEG) intraocular latanoprost implant for reducing elevated intraocular pressure. The implant can be configured as a film about 100 μm to about 500 μm thick and about 2 to about 6 mm in diameter when unrolled, or an extruded filament with a diameter between about 500 μm to 1.5 mm and a length between about 5 μm to about 10 mm. Either implant is inserted into the eye of an individual via a needle to provide for extended release of latanoprost for at least 30 days. The implant requires a doctor to put it in place and it cannot be easily removed in the event of an allergic reaction.

U.S. Patent Application Publication 2004/0241207 describes a contact lens with embedded drug nanoparticles having a particle size less than about 200 nm. The embedded drug is capable of diffusion into and migration through the contact lens and into the post-lens tear film when the contact lens is placed on the eye. The technology has significant challenges both in manufacturing and maintaining the refractive power of the lenses due to light deflection occurring as a result of embedded drug particles.

SUMMARY

To address the issues set forth above, a nanostructured biocompatible wafer for placement in the conjunctival cul-de-sac is provided. The wafer contains a tissue-reactive mucoadhesive polymer and a mesh formed of a plurality of polymer fibers. The tissue-reactive mucoadhesive polymer is coated on the wafer or intercalated with the fibers. The wafer has a thickness of 0.05 mm to 0.5 mm, a hydrated flexural modulus less than 25 MPa, and an oxygen permeability of 15 Dk to 30 Dk. The mesh has a pore size of 50 nm to 1000 nm, and the polymer fibers have a diameter of 100 nm to 1500 nm.

Also provided is a method for treating glaucoma, an ocular surface disorder, or an ocular surface infection by placing the nanostructured biocompatible wafer described above also containing a drug into the conjunctival cul-de-sac of a subject and maintaining the nanostructured biocompatible wafer in the conjunctival cul-de-sac for a period of 2 weeks to 6 months.

Alternatively, an injectable sustained-release formulation for treating an ocular disorder is disclosed. The formulation includes a drug contained within a plurality of microparticles. The microparticles are formed of a biodegradable polymer, and are coated with a tissue-reactive compound. The coated microparticles (i) have a size of 1 μm to 40 μm, (ii) contain 20% to 30% by weight of the biodegradable polymer, and (iii) contain 5% to 20% by weight of the tissue-reactive compound.

Also disclosed is a method for treating an ocular disorder by injecting the sustained release formulation described above into the eye of a subject suffering from an ocular disorder.

The details of one or more embodiments of the invention are set forth in the drawings and description below. Other features, objects, and advantages of the invention will be apparent from the description, the drawings, and from the claims. The contents of all documents cited herein are hereby incorporated by reference in their entirety.

BRIEF DESCRIPTION OF THE DRAWINGS

The invention description below refers to the accompanying drawings, of which:

FIG. 4D is a plot of an in-vitro release profile of brinzolamide from a nanostructured biocompatible wafer;

FIG. 5A is a cross-sectional view of a biaxial fiber for incorporation into a nanostructured biocompatible wafer and for manufacturing microparticles for an injectable sustained release formulation;

FIG. 5B is a cross-sectional view of a tri-annular fiber for incorporation into a nanostructured biocompatible wafer and for manufacturing microparticles for an injectable sustained release formulation; and FIG. 5C is a cross-sectional view of an alternative tri-annular fiber for incorporation into a nano structured biocompatible wafer and for manufacturing microparticles for an injectable sustained release formulation.

DETAILED DESCRIPTION

Definition of Terms

Figure 1A:
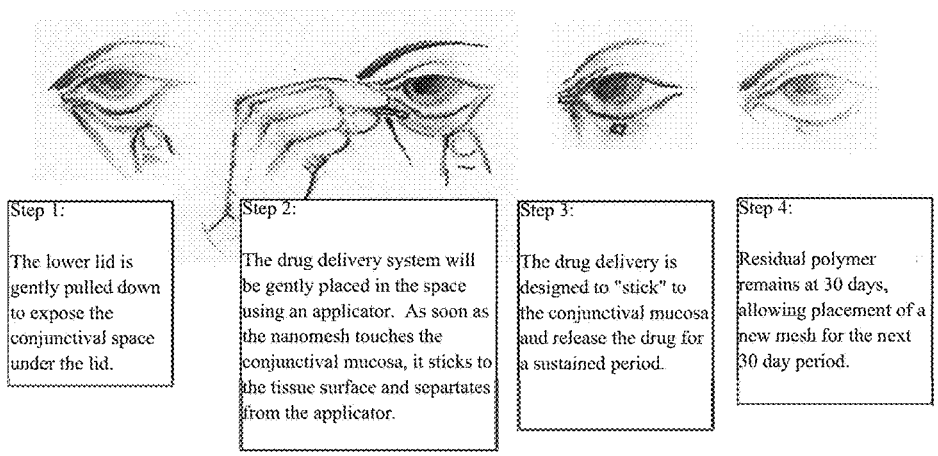
FIG. 1A is an illustration of a method for placing of a drug-releasing mesh in the eye.

"Biodegradable polymer" means a polymer or polymers which degrade in vivo, and wherein erosion of the polymer or polymers over time occur concurrent with, or subsequent to release of the therapeutic agent. The terms "biodegradable" and "bioerodible" are used interchangeably herein. A biodegradable polymer may be a homopolymer, a copolymer, or a polymer containing more than two different polymeric units. The polymer can be a gel or hydrogel type polymer.

"Ocular condition" means a disease, ailment, or condition which affects or involves the ocular region. Broadly speaking, the eye includes the eyeball and the tissues and fluids which constitute the eyeball, the periocular muscles, and the portion of the optic nerve which is within or adjacent to the eyeball.

An anterior ocular condition is a disease, ailment, or condition which affects or which involves an anterior, i.e., front of the eye, ocular region or site, such as a periocular muscle, an eye lid, or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens, or the lens capsule and blood vessels and nerve which vascularize or innervate an anterior ocular region or site. Thus, an anterior ocular condition can include diseases such as aphakia, pseudophakia, astigmatism, blepharospasm, cataract, conjunctival diseases, conjunctivitis, corneal diseases, corneal ulcer, dry eye syndromes, eyelid diseases, lacrimal apparatus diseases, lacrimal duct obstruction, myopia, presbyopia, pupil disorders, refractive disorders, and strabismus.

A posterior ocular condition is a disease, ailment, or condition which primarily affects or involves a posterior ocular region or site such as choroid or sclera (in a position posterior to a plane through the posterior wall of the lens capsule), vitreous, vitreous chamber, retina, optic nerve, optic disc, and blood vessels and nerves which vascularize or innervate a posterior ocular region or site. Thus, a posterior ocular condition includes diseases such as acute macular neuroretinopathy, Behcet's disease, choroidal neovascularization, diabetic uveitis, histoplasmosis, infections such as fungal or viral infections, macular degeneration (e.g., acute macular degeneration, non-exudative age related macular degeneration and exudative age related macular degeneration), edema (e.g., macular edema, cystoid macular edema and diabetic macular edema), multifocal choroiditis, ocular trauma which affects a posterior ocular site or location, ocular tumors, retinal disorders such as central retinal vein occlusion, diabetic retinopathy, proliferative diabetic retinopathy, proliferative vitreoretinopathy (PVR), retinal arterial occlusive disease, retinal detachment, uveitic retinal disease, sympathetic ophthalmia, Vogt Koyanagi-Harada (VKH) syndrome, uveal diffusion, a posterior ocular condition caused by or influenced by an ocular laser treatment, posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, and retinitis pigmentosa.

"Ocular region" or "ocular site" means any area of the eyeball, including the anterior and posterior segment of the eye.

"Conjunctival cul-de-sac" is the conjunctival region in the lower eye socket that is exposed when the bottom eyelid is pulled downward.

"Tissue engineered" refers to polymers that integrate themselves into the tissues with which they come in contact thereby embedding the therapeutic agent therein into the tissue for sustained release activity.

"Sustained release" or "controlled release" refers to the release of at least one therapeutic bioactive agent from an implant at a predetermined rate. Sustained release implies that the therapeutic bioactive agent is not released from the implant sporadically in an unpredictable fashion and does not "burst" from the implant upon contact with a biological environment unless specifically intended to do so. However, the term "sustained release" as used herein does not preclude a "burst phenomenon" associated with deployment.

"Therapeutically effective amount" means the level or amount of agent needed to treat an ocular condition, or reduce or prevent ocular injury or damage without causing significant negative or adverse side effects to the eye or a region of the eye.

"Glaucoma" is a disease of the anterior chamber. Intraocular pressure (IOP) variation appears to be an independent risk factor for glaucomatous damage.

"Electrospinning" refers to a process that generates polymer fibers to generate a weave, or a mesh-like material. Electrospinning uses an electrical charge to draw very fine (typically on the micro or nano scale) fibers from a liquid.

"Microencapsulation" refers to a process that generates polymeric encapsulates containing a drug.

Embodiments

Disclosed is a drug-containing nanostructured biodegradable, biocompatible, flexible mesh wafer that can be placed by a caregiver or a patient into the patient's conjunctival cul-de-sac (see FIG. 1A) to deliver a medication short-term or long-term. The drug release rate can be modulated to achieve therapeutic drug concentrations at the target tissue to persist for at least 1 week, 1 month, 2 months, 3 months or 6 months. The nanomesh wafer resulted from a bioengineering approach to administer medications to the eye, unlike the related art discussed above. The thickness of the nanomesh wafer, its flexural modulus, and its oxygen permeability are important aspects for long term biocompatibility, in addition to its sustained release profile and timely biodegradation. Additionally, the interconnected nano-sized pores and mesh structure of this drug delivery system are conduits for fluid flow in, around, and through the wafer, much like an extra-cellular matrix. This allows the wafer to be highly hydrated, reducing foreign body reaction and conjunctival surface damage.

The nanomesh wafer can be formed of monolithic, co-axial, or tri-axial fibers, with one drug or multiple drugs, with varied compositions that control biodegradation and drug release. See FIGS. 5A, 5B, and 5C. One important aspect of the nanomesh wafer is the presence of components in the mesh that crosslink with other components in the mesh as well as with the tissue to hold the device in-place long term. Another important aspect of the mesh is the inclusion of membrane-compatible components that make the nanomesh wafer highly biocompatible with ocular tissue.

The nanomesh wafer solves the drawbacks of eye-drop delivery of ophthalmic medications described above. It is a platform sustained-release drug delivery system and can be used to deliver drugs to treat disorders of the anterior chamber and ocular surface. These include but are not limited to, corneal keratitis, allergic conjunctivitis, post-surgical inflammation, (cataract, glaucoma, corneal transplant), blepharitis, corneal tear/injury, dry eye, fungal infections, and corneal methicillin resistant *Staphylococcus aureus* (MRSA) infection, and glaucoma.

Dimensionally, the nanomesh wafer is appropriately sized to fit into the conjunctival cul-de-sac. It is flexible and contains ingredients that impart flexibility to render it biocompatible with the tissue surface. As such, the modulus of the insert is less or equal to that of the tissue surface. The nanomesh wafer can be placed on the surface of the eye on the conjunctiva. It is neither an injectable nor an implant. It is an insert that rapidly hydrates and adheres to the ocular surface. The nanomesh wafer is not placed on the cornea and does not disrupt the visual field.

The size of the nanomesh wafer can be appropriately sized to fit the conjunctival space of the human eye. Preferably, the size of the nanomesh wafer is 0.1±0.05 mm thick, 5±0.5 mm wide, and 10±0.5 mm long.

Figure 1B:
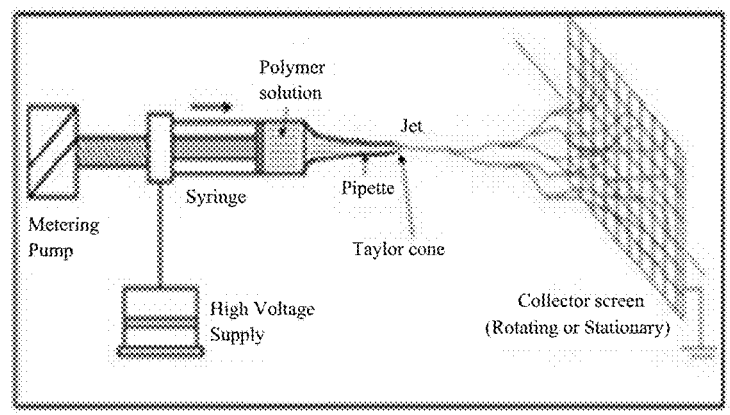
FIG. 1B is a schematic of a method to fabricate the mesh shown in FIG. 1A.
Figure 1C:
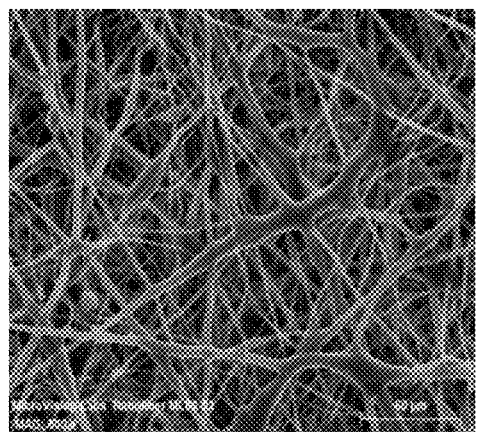
FIG. 1C is a scanning electron micrograph (SEM) of a travoprost-containing nanostructured biocompatible wafer produced by electrospinning.
Figure 1D:
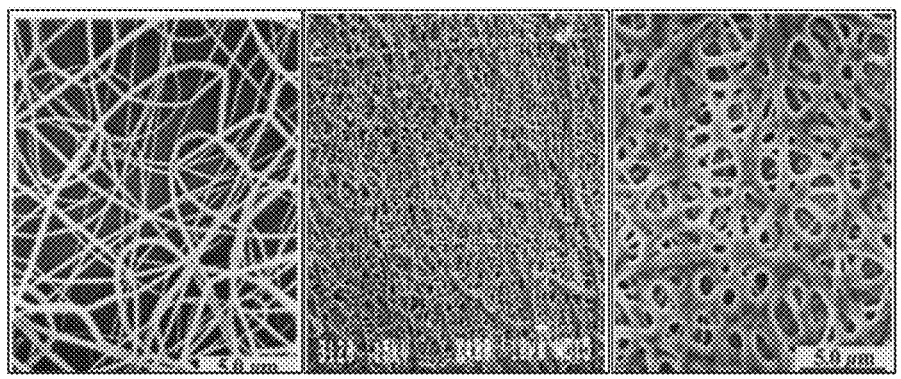
FIG. 1D are SEMs of travoprost-containing nanostructured biocompatible wafers produced using three different exemplary process conditions.
Figure 1E:
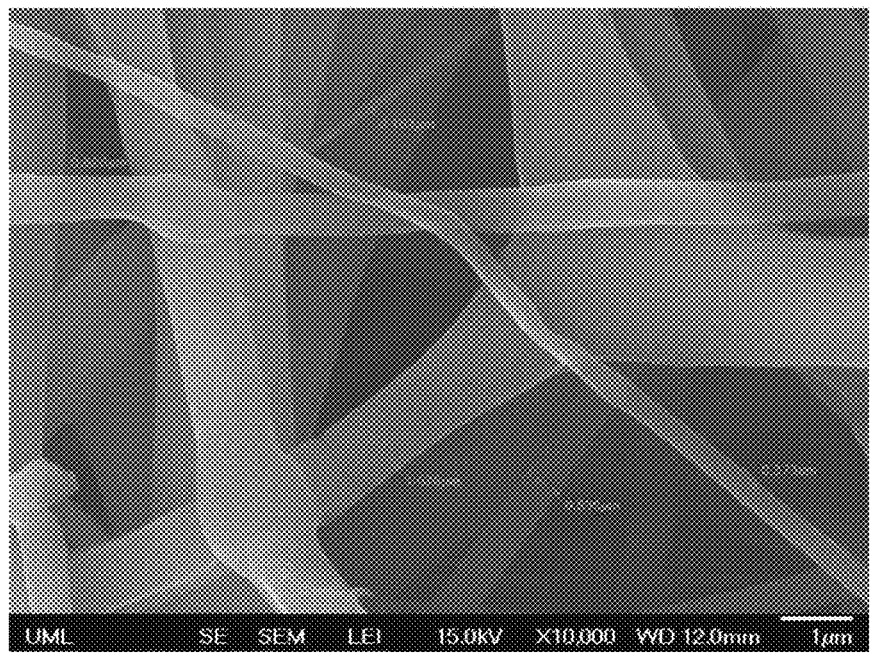
FIG. 1E is a magnified SEM of a travoprost-containing nanostructured biocompatible wafer showing interconnected conduits of the mesh wafer.

Structurally, the wafer is a drug-containing nanostructured mesh that has interconnecting open-celled pores. See FIGS. 1C, 1D, and 1E. The mesh size of the interconnecting pores can be 100-200 nm, 200-300 nm, or 300-600 nm. Alternatively, the mesh size is a combination between 100-600 nm. The thickness of the nanomesh wafer is between 0.05-0.5 mm, preferably between 0.05-0.1 mm.

The nanostructured wafer can be biodegradable, and can be formed of, but not limited to the polymers polylactide-co-glycolide (PLGA), polylactic acid (PLA), polycaprolactone (PCL), poly(trimethylene carbonate), poly(amino acids), hyaluronic acid, polyethylene glycol (PEG), polyethylene oxide-polypropylene oxide-polyethylene oxide triblock copolymer, PEG-stearate, PEG-distearoyl-sn-glycero-3-phosphoethanolamine, lecithin, xanthan, polyvinylalcohol, polyvinylpyrrolidone, albumin, collagen, or any combination of these biodegradable polymers.

Preferably, the biodegradable polymers are available commercially and approved for human use.

In another embodiment, the nanostructured wafer is not biodegradable. This wafer can be formed of polymers having high oxygen permeability. For example, polysiloxanes and polymethylmethacrylate (PMMA) polymers can be used to form the nanostructured wafer. The non-biodegradable wafer can be removed intact from the conjunctival cul-de-sac at any time during or following treatment.

In another embodiment, the nanostuctured wafer is formed of a mix of biodegradable and non-biodegradable polymers. The polymers can be any of those listed in the preceding paragraphs.

The nanostructured wafer can be produced to have a hydrated flexural modulus similar to that of conjunctival tissue. Preferably the hydrated flexural modulus of the wafer is between 10-25 mPa.

In another aspect, the nanostructured wafer can have high oxygen permeability. The oxygen permeability can be 15 Dk to 30 Dk (e.g., 15, 20, 25, and 30). In a particular embodiment, the oxygen permeability of the wafer is 25 Dk.

Figure 2A:
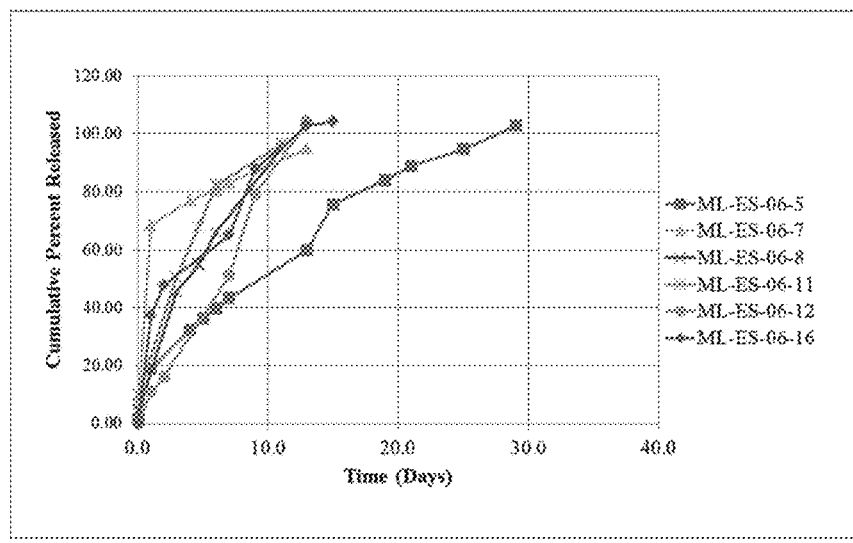
FIG. 2A is a plot of an in-vitro release profile of travoprost from a nanostructured biocompatible wafer in phosphate buffer at 37° C.
Figure 2B:
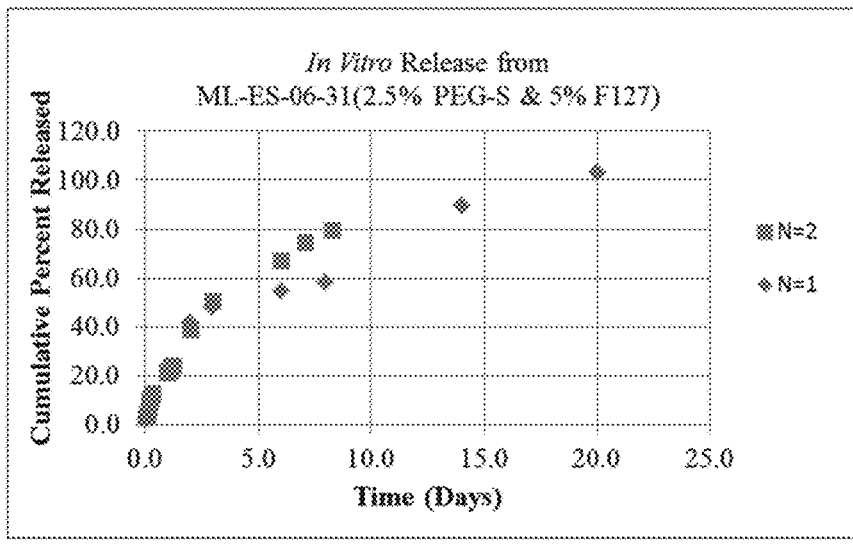
FIG. 2B is a plot of release kinetics of travoprost from a nanostructured biocompatible wafer.
Figure 2C:
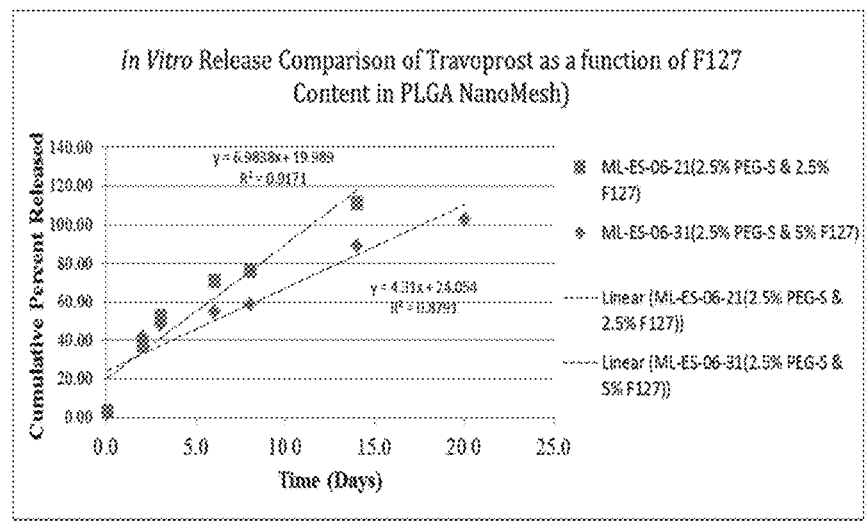
FIG. 2C is a plot of release kinetics of travoprost from nanostructured biocompatible wafers of differing composition.
Figure 2D:
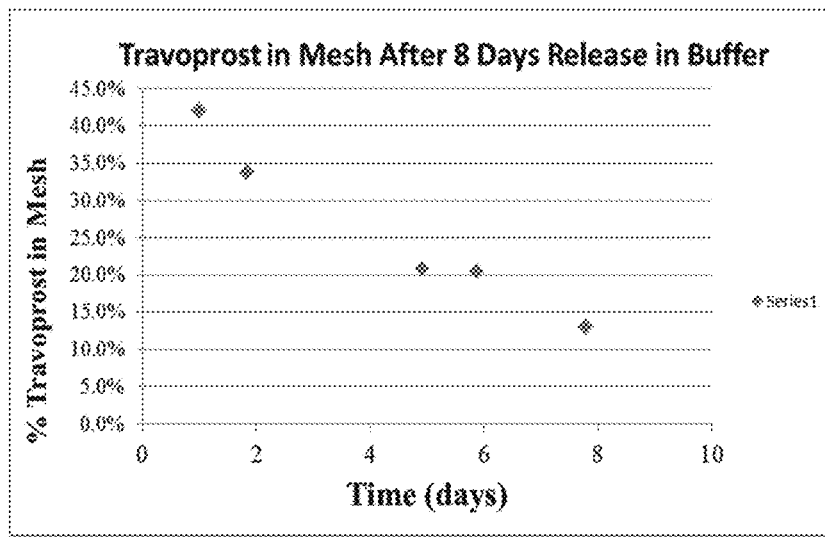
FIG. 2D is a plot of travoprost amount remaining in a nanostructured biocompatible wafer versus time in release buffer.

The drug incorporated in the nanomesh will be contained in the biodegradable portions. To incorporate, the drug and the biodegradable polymer are dissolved in a suitable organic solvent such as ethyl acetate, ethanol or acetone and electrospun using optimized conditions on to a collector plate. The biodegradable polymer or polymer blend releases drug as the matrix degrades and as the drug finds diffusive paths through the matrix. The rate of degradation is modulated by the composition of the nanomesh wafer. See FIGS. 2A, 2B, and 2C.

Another aspect of the nanomesh wafer is that it is designed to bind to the ocular conjunctiva either by ionic bonding or by light complexation of proteins on the tissue surface with moieties on the nanomesh. As such, these moieties may be thiolated, or aminated.

The nanomesh wafer can contain mucoadhesive tissue-reactive components that have reactive groups that react with the ocular tissue surface. Mucoadhesive properties can be incorporated by inclusion of a charged polymer on the surface or intercalated with the drug-loaded fibers. The charged polymer can be, but is not limited to, xanthan gum, guar gum, chitosan, hyaluronic acid, alginate, xyloglucans, polycarbophil, polyacrylic acid, tamarind seed polysaccharide, or a polyamino acid, such as polylysine.

The nanomesh wafer can be applied as a dry drug-containing system, which will rapidly hydrate and adhere to the conjunctival tissue. In another embodiment, the wafer is applied moist in a fully hydrated state. The hydrating liquid can be, but is not limited to an albumin solution, a solution containing hyaluronic acid, or saline.

In another embodiment, the nanomesh can be drug-free and utilized as a wound healing aid.

Additionally, the nanomesh wafer can contain more than one distinct layer, one over the other, with each layer imparting specific functional properties to the wafer. The layers may be intercalated within each other like a "weave," imparting properties of mechanical strength, flexibility, or biocompatibility. For example, one layer can contain a drug in a polymer matrix and the other layer can contain the tissue-reactive ingredient. One layer may contain one drug and another may contain another drug. For example, an antibiotic and an anti-inflammatory steroid may be incorporated in separate layers with different release rates engineered for each drug.

The nanostructured mesh wafer described above can be produced by co-axial fiber spinning. In this embodiment, the fiber produced by this process, as shown in FIG. 5A, will be a co-axial filament, with the core (2) being the drug-containing biodegradable polymer and the outer layer (1) being a mucoadhesive polymer. In another embodiment illustrated in FIG. 5B, the fiber can be produced as a tri-axial filament having an inner drug-containing polymer (5), a second drug-containing polymer (4) surrounding the inner drug-containing polymer (5), and an outer polymer layer (3) formed of a mucoadhesive polymer. Alternatively, a tri-axial filament can be prepared that contains three drug-containing cores (7, 8, 9) embedded in a layer (10) of a mucoadhesive polymer that can also contain a drug.

In another embodiment of the nanomesh wafer, biodegradable drug-containing microspheres can be sprayed onto the mesh to create a microsphere/mesh composite, to achieve the requisite drug release properties.

The nanomesh wafer can be prepared through various methods of fiber spinning. For example, the fibers can be formed by electrospinning, electrospraying, melt extrusion, solvent extrusion, micro-weaving, melt spinning, wet spinning, fiber drawing, or a combination of these techniques. The nanomesh wafer can be formed by a combination of solution casting and fiber spinning. The layers may be formed by using a fine micronized ultrasonic spray of a solution containing a mucoadhesive polymer described above over a previously formed nanomesh mat. The ultrasonic spray will form a monolayer of the mucoadhesive polymer on the nanomesh wafer. The mesh can also be produced by 3D printing techniques. The nanomesh wafer can be produced in rolls or sheets, dried under vacuum, and cut to size.

In the case of glaucoma therapy, the nanomesh wafer can be manufactured from polymeric materials that quickly meld with the conjunctival tissue of the conjunctival cul-de-sac. Upon insertion, the drug-containing wafer is designed to hydrate and mold itself to the conjunctiva and begin sustained release of an anti-glaucoma therapeutic through the cornea and into the anterior chamber of the eye.

The nanomesh wafer described above can be preservative-free to avoid preservative-induced toxicity after long-term use. In an alternative embodiment, the nanomesh wafer contains a preservative.

The wafer can be sterilized and packed in a foil sterile pack that is impermeable to moisture and gases. For example, the nanomesh wafer can be sterilized by ethylene oxide, gamma irradiation, or UV light. In another example, each component of the wafer prior to forming fibers is sterile filtered and the nanomesh wafer is formed aseptically.

The drug incorporated into the nanomesh wafer can be a small molecule or a macromolecule such as a protein, a peptide, and a nucleic acid.

In a particular embodiment, the drug incorporated into the nanomesh wafer can be a glaucoma drug. For example, the drug can be, but is not limited to, a prostaglandin, a prostaglandin analogue, and a prostamide.

In one aspect, the prostaglandin incorporated into the nanomesh can be latanoprost, tafluprost, unoprostone, or bimatoprost.

In addition to the drugs listed above, any drug that lowers IOP can be incorporated into the nanomesh wafer. For example, brinzolamide and timolol can be incorporated into the nanomesh wafer.

The nanomesh wafer can contain a total amount of prostaglandin, per wafer, from 0.5-1000 µg, e.g., 0.5-50 µg, 1-200 µg, 50-100 µg, 100-200 µg, and 200-1000 µg. Preferably, the amount of prostaglandin in the wafer will be in the range of 100-350 µg.

In a specific embodiment, the nanomesh wafer can be used in a method for treating glaucoma by the sustained release of travoprost for 30 days. See FIGS. 2A and 2B. In another embodiment, the nanomesh wafer can be used to treat glaucoma by sustained release of brinzolamide for 30 days. See FIG. 4D. In another embodiment, the glaucoma medication may be released for a longer period of time, e.g., 60 days. In another embodiment, the glaucoma medication may be released for 90 days, 120 days, or 180 days. The nanomesh wafer can be manufactured to modulated travoprost release such that a "burst" is followed by sustained release. In one embodiment, a particular release rate of travoprost can be achieved by changing the composition of the wafer. See FIG. 2A and EXAMPLE 1 below.

In another embodiment, the wafer may contain two anti-glaucoma drugs in combination to achieve the required therapeutic effect. For example, the two glaucoma drugs can be brinzolamide and travoprost. In another embodiment, the two drugs are brinzolamide and brimonidine tartrate.

In another example, the nanomesh wafer can contain both an anti-inflammatory and an anti-microbial. Preferably, the nanomesh wafer contains loteprednol etabonate and tobramycin.

The duration of drug release can be optimized to release the drug in the range between, e.g., 1-7 days, 1-15 days, 1-30 days, 1-45 days, 1-60 days, 1-75 days, 1-90 days and 1-180 days.

The absolute amount of drug per nanomesh wafer can be between 0.001-0.1 µg, 0.01-0.1 µg, 0.1-0.5 µg, 0.5-1 µg, 1-10 µg, 10-100 µg, 100-500 µg, 500-1000 µg, 1000-2000 µg, 2000-5000 µg, and 5000-10000 µg.

As mentioned above, drug-containing nanomesh wafers can be used to treat infections of the eye and disorders related to microbial infections, such as conjunctivitis, keratitis, blepharitis and rosacea. Ophthalmic antibiotics are available from a variety of drug classes including aminoglycosides, macrolides, polypeptides, quinolones, and sulfonamides. In addition, many are available as combination products with other antibiotics or corticosteroids. Any of these existing approved ophthalmic antibiotics can be loaded into the nanomesh wafer described herein.

The antimicrobial incorporated in the nanomesh wafer described above can be, but is not limited to moxifloxacin, azythromycin, mupirocin, erythromycin, ciprofloxacin, netilmycin, besifloxacin, gatifloxacin, gentamycin sulfate, levofloxacin, ofloxacin, sulfacetamide sodium, tobramycin, bacitracin zinc, Polymyxin B sulfate, neomycin, and neomycin sulfate.

The nanomesh wafer offers advantages over current ocular antimicrobial formulations. More specifically, the nanomesh wafer described above can efficiently deliver a small dose of antibiotic to ocular tissues at concentrations greater than the minimum bacteriocidal concentration to effectively eliminate the bacteria. Lower concentrations of drug that are less than the minimum bacteriocidal concentration, such as the doses achieved by antibiotic eye drops can lead to the bacteria evolving to become drug resistant. This mode of delivery can lower the incidence of MRSA. In one embodiment, the nanomesh wafer contains mupirocin, a drug utilized to treat MRSA in nasal linings.

In another aspect, the nanomesh wafer can contain an anti-viral drug. The anti-viral incorporated in the nanomesh can, in a particular embodiment, be used to treat herpes simplex virus (HSV). The anti-viral used to treat HSV can be, e.g., acyclovir, valacyclovir, and famciclovir. The anti-viral incorporated in the nanomesh can be used to treat viral conjunctivitis.

The drug incorporated in the nanomesh wafer can be used to treat ocular rosacea. Patients displaying clinical symptoms of ocular rosacea typically also have dermal rosacea. Ocular rosacea is characterized by redness, crusting of the eyelid, itching and irritation. Currently, there is no treatment. The drug can be a therapeutic that is currently in testing or under FDA approval for dermal rosacea. The drug can be one that is used to lower inflammation in tissues. The drug can be oxymetazoline hydrochloride, cetirizine hydrochloride, fluticasone propionate, fluticasone furoate. The drug used to treat ocular rosacea can be an anti-allergy medication.

The drug incorporated in the nanomesh can be used to prevent or treat ocular pain. In this example, the drug incorporated in the nanomesh is an analgesic. The drug is selected from bromfenac sesquihydrate, amfenac, nepafenac, aspirin, ibuprofen, ketorolac tromethamine, or any other drug that has analgesic and anti-inflammatory activity.

Alternatively, the drug incorporated in the nanomesh can be an anesthetic. The drug can be but is not limited to lidocaine and novocaine.

The nanomesh can be formulated to contain wound healing components. Specifically, the nanomesh may contain purified 1→3 beta glucan, or 1→6 beta glucan. In one example, the nanomesh contains purified tamarind seed polysaccharide. In another example, the nanomesh contains a combination of albumin, lecithin, collagen, hyaluronic acid, beta glucan, and tamarind seed polysaccharide.

In a further example, the nanomesh can contain components that will lubricate the ocular surface. Examples of such components are xanthan gum, hyaluronic acid, and tamarind seed polysaccharide, or combinations thereof. In another example, the nanomesh can contain lipids and a mucoadhesive.

In one example, the nanomesh can be used to treat dry eye in a sustained fashion. Furthermore, the nanomesh can contain a dry-eye medication, such as cyclosporine.

In another embodiment, the nanomesh wafer can contain an anti-inflammatory. The anti-inflammatory incorporated in the nanomesh includes but is not limited to loteprednol etabonate, fluticasone propionate, dexamethasone, dexamethasone phosphate, prednisolone, prednisolone phosphate, budesonide, triamcinolone acetonide, indomethacin, diclofenac, nepafenac, bromfenac, pranoprofen, and any other drug that may have anti-inflammatory activity.

Figure 4A:
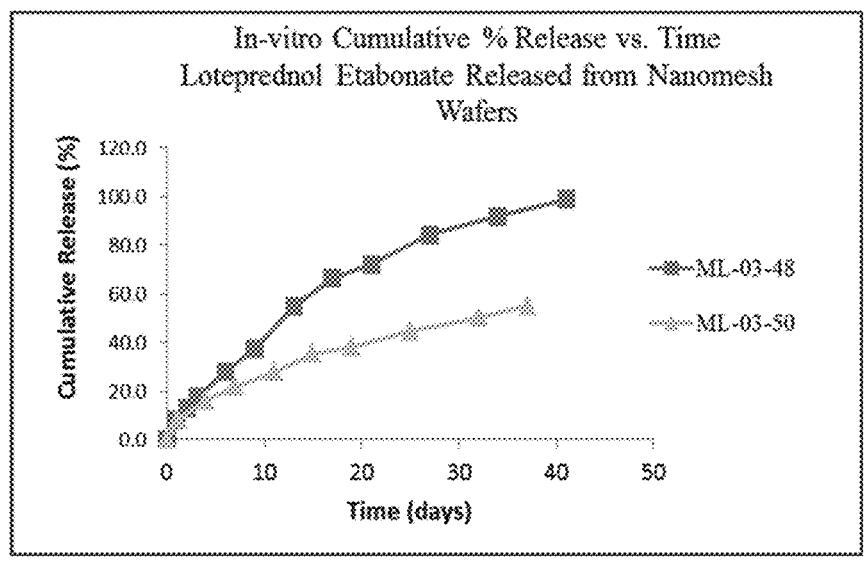
FIG. 4A is a plot of an in-vitro release profile of loteprednol etabonate from a nanostructured biocompatible wafer.
Figure 4B:
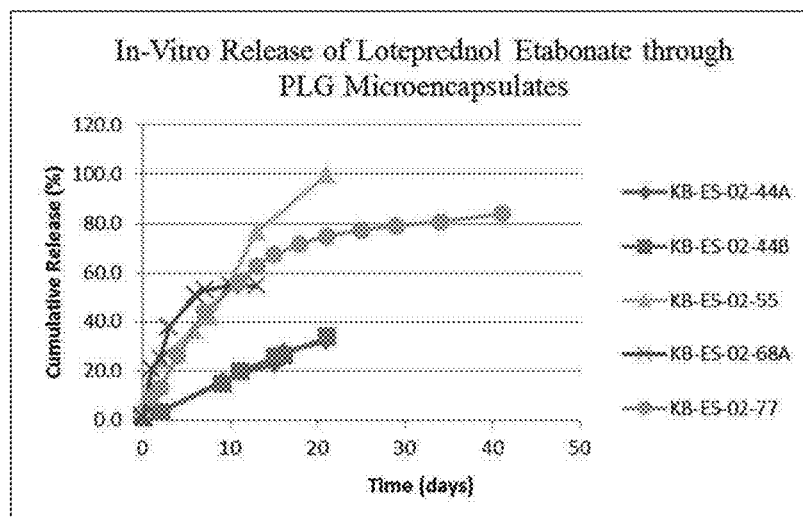
FIG. 4B is a plot of an in-vitro release profile of loteprednol etabonate from microparticles of an injectable sustained release formulation.
Figure 4C:
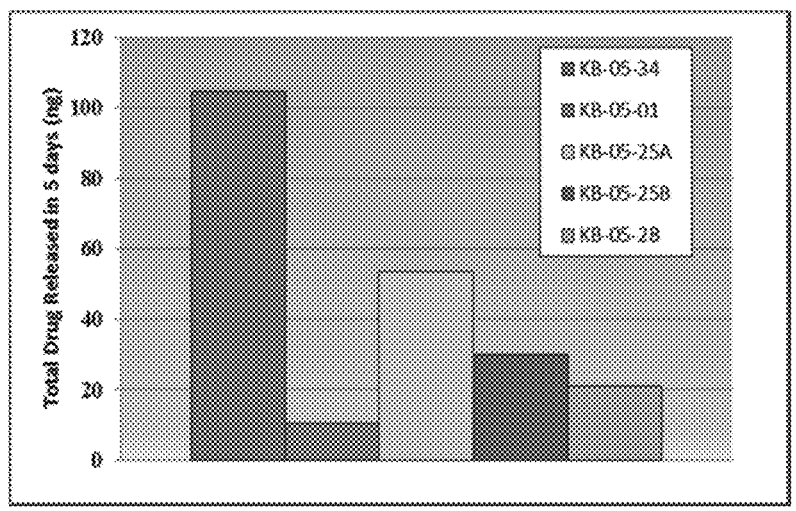
FIG. 4C is a bar graph showing the amount of loteprednol etabonate released from microparticles of an injectable sustained release formulation as a function of microparticle size.

In a particular embodiment, the nanomesh wafer can be used to treat allergic conjunctivitis by sustained release of loteprednol etabonate for 20-60 days, as shown in FIG. 4A.

In another aspect, the nanomesh contains an anti-fungal medication. Itraconazole, Posaconazole, Voraconazole and other anti-fungal compounds known to have anti-fungal activity can be incorporated into the nanomesh wafer.

The nanomesh wafer is designed to be non-irritating to the surface of the eye. A novel correlation of wafer thickness to ocular irritation is disclosed. See EXAMPLE 1 below. For the wafer to be non-irritating, it should be <0.5 mm thick. The non-irritating nature of the wafer is also a function of its composition and flexibility.

In addition to the nanomesh wafer, an injectable sustained-release formulation containing micro- or nano-sized drug encapsulates for treating ocular disorders is disclosed. The injectable sustained-release formulation can be used to deliver both front-of-the-eye medications and back-of-the-eye medications. For front-of-the-eye disorders, the sustained-release formulation is injected into the tissue in the conjunctival cul-de-sac via a syringe to obviate the need for multiple eye-drop administrations. For posterior segment disorders, medication-containing encapsulates are injected into the vitreous, sub-retinal space, supra-choroidal space, sub-Tenon's space or any other space known to the clinician to access the posterior ocular space. The formulation is not limited to treating disorders of the eye. The formulation can be used to treat a multitude of conditions and disorders in different tissues, e.g., the eye, skin, wounds, urogenital tract, brain, pulmonary, and nose.

The injectable sustained-release formulation contains encapsulates that are precisely engineered to a defined size, shape, and specific internal microstructure. Size, shape, and microstructure are modulated to release a drug or multiple drugs from a multi-layered matrix at rates requisite to achieve a therapeutic effect over a specified period of time, e.g., fast and sustained, while maintaining drug concentrations below levels known to cause toxic symptoms. The release of drug is controlled by composition, size, and size distribution and internal microstructure of the encapsulates.

The injectable encapsulates are micro- or nano-sized encapsulates that are (a) injectable through a 27 G-31 G needle, (b) remain dispersed in tissue or tissue fluids such as the vitreous, i.e., minimal clumping, and (c) display a sustained and predictable drug release.

The internal microstructure of the encapsulates is designed to be solid with the release rate controlled by a combination of diffusion and degradation. The surface of the encapsulates has been designed to be smooth, with a surface coating that supports good flow characteristics.

The internal microstructure of the encapsulates can consist of concentric rings (cross-sections shown in FIGS. 5A and 5B), with each ring consisting of a polymer composition that is engineered to release a drug at a specific rate. The internal microstructure of the delivery system can be bi-axial, with two concentric rings characterizing each axis (See cross-sectional view, FIG. 5A), creating a core matrix and a corona matrix, each containing a drug. Alternatively, the matrix can be monolithic, with a single homogeneous composition with incorporated drug. Each concentric ring can be formed of a different matrix. The microstructure can also be multi-axial, with three or more concentric rings each containing different drugs and/or matrix components. See a cross-section schematic in FIG. 5B. The internal microstructure of the encapsulates can be co-axial with multiple axes within a larger axis (FIG. 5C). The shape of the encapsulates can be cylindrical, disc-like, spherical, square, and rectangular, depending upon the process utilized to fabricate the encapsulates. The internal cross-sectional microstructure of the encapsulates is multi-layered, with the architecture and thickness of each layer specific and defined. The composition of each layer is varied by varying the composition of polymer blends used to fabricate each layer. The composition of the polymer blend in each layer can be varied to modulate the release of drug.

The microstructure of the encapsulates can consist of localized regions of one polymer composition (discontinuous phase) contained in another polymer composition that comprise the continuous phase of the matrix (see FIG. 5C).

In one embodiment, the first layer consists of a first drug incorporated in a polymeric matrix, the composition of which is engineered to release the first drug at a certain rate (rate 1). The second layer consists of a second drug incorporated in a polymer matrix, the composition of which is engineered to release the second drug at another rate (rate 2). In one example, the matrix in layer 1 containing the first drug can release the drug within hours, weeks, or months, while the matrix in layer 2 containing the second drug can also release the drug within hours, weeks, or months.

The drug may be the same in each matrix. Alternatively, the drug may be different for each matrix.

The size of the encapsulates can be less than 100 nm, between 10-100 nm, 101-200 nm, 201-400 nm, 401-600 nm, 601-800 nm, 801-1000 nm, 1 micron-10 microns, 10-20 microns, 20-30 microns, 30-40 microns, 40-50 microns, 50-60 microns, 60-70 microns, 70-80 microns, 80-100 microns, 100-150 microns, 150-300 microns, 300 microns-1000 microns. If rod-like, in one embodiment, the aspect ratio of the encapsulates can be 1:1, 1:2, 1:3, 1:4, 1:5, 1:6, 1:7, 1:8, 1:9 and 1:10. The shape of the encapsulates may be rod-shaped, wafer-like, discoid, cuboid, cylindrical and rectangular.

The matrices forming the encapsulates can be biodegradable, with the rate of biodegradation modulated by combining various biodegradable polymers. The biodegradable polymers can be, but are not limited to, polydioxanone, PLG, PCL, poly(caprolactone-co-glycolide), poly(esteramide), poly(trimethylene carbonate), poly(ethylene oxide-co-lactide), polyethylene glycol and combinations thereof. In another embodiment, the matrices may be blended with polymers and excipients that lend biocompatibility such as PVA, hyaluronic acids of different molecular weights, chitosans of various molecular weights, PEG-cholesterols, albumins, lecithins, phosphatidyl choline, phosphatidic acid, lauric acid, stearic acid, myristic acid, sorbitans, PEG-castor oils, capric acid, vitamin E-PEGs, PEG-fatty acids and combinations of these ingredients.

To lessen or prevent aggregation in-vivo, the surface characteristics of the encapsulates can be optimized to be non-adherent to each other and to the tissue space.

One way to enhance dispersion into the tissues is to optimize the surface of the encapsulates with coatings that provide "slippage" into the crevices of the tissues. To that end, coatings that are PEG-based, or polysiloxane-based, among others, can be used. Molecules such as silicones, lecithins, phosphatidyl cholines, albumins, and collagen can also be used for this purpose. The dispersion of the encapsulates in the injectable formulation will result in efficient dispersion of the drug within the tissue.

The encapsulates can be prepared by melt extrusion or melt spinning techniques through mono-axial, di-axial, or tri-axial tube needles, following by cutting to a precise size.

In another embodiment, the drug molecules being released are identical, with each matrix layer releasing the drug at a different rate, to achieve for example, a burst initial release of drug from one layer, followed by a slower sustained release of drug from another layer.

Other methods of fabricating the encapsulates are 3D printing, electro-spinning through co-axial needles followed by cutting the filaments to size, and formation of core-shell microspheres by water-oil-water, oil-water, or oil/oil techniques.

Drugs can be encapsulated in biodegradable micro spheres by dissolution of the drug and the polymer in an organic solvent, then generating uniform "droplets" by ultrasonic spraying into a solvent system that precipitates the polymer-encapsulated drug into spheres. The size can be controlled by controlling the size of the droplets. The precipitating bath may contain a silicone polymer, or an ingredient that incorporates a slippage inducing excipient onto the surface of the microspheres. The precipitating bath may contain a water-soluble polyurethane with emulsifying properties.

In another example of efficient and beneficial dispersion, the drug-containing encapsulates are injected into the subchoroidal space of the eye. The encapsulates are designed to disperse and spread in this space surrounding the retina. Drug from the matrices in the encapsulates can be released into the retina in a uniform flux. In another example where continued dispersion is beneficial, the encapsulate can be manufactured to remain discreet and punctate, releasing a predicted amount of drug per unit time.

The encapsulates in the injectable formulation can be surface-coated with excipients that are known dispersants of particles to minimize clumping after administration. These excipients include, but are not limited to, PEG40-stearate, PEG-lecithin, polymers of the structure PEO-PPO-PEO, glycocholic acid, and cholic acid. The coating on the encapsulates may be positively charged, negatively charged, or neutral.

In another example, the encapsulates can be surface-coated with silicones by ultrasonic spraying. In another method to prepare "non-stick" injectable encapsulates, surface coating may be added by a washing step that contains injectable silicone and ethanol, enabling deposition of a very fine layer of silicone. Only injectable silicones are utilized for this purpose. Microspheres that have been coated with silicones will "roll" when injected and will immediately disperse.

In another example, the encapsulates can be spray-coated with silica, titanium dioxide, albumin, or polyvinyl alcohol.

In one example, the encapsulates are dispersed in a biocompatible gel such as hyaluronic acid, albumin, collagen, or combinations thereof. In another example, the encapsulates are dispersed in a synthetic simulated fluid.

In another example, the encapsulates are dispersed in a biological fluid, such as serum plasma extracted from blood stock, a simulated ocular fluid, or amino acids and polyamino acids found in biological systems.

The injectable sustained-release formulation can be delivered intravenously, either targeted or non-targeted. In this regard, the encapsulates in the formulation can be surface coated with a targeting antibody.

In another embodiment, the surface characteristics of the encapsulates can be modified to encourage phagocytosis, or to elicit an appropriate immune reaction. For example, the injectable sustained-release formulation can be a vaccine, either therapeutic or prophylactic. In that case, the encapsulates in the formulation will be targeted to antigen presenting cells to elicit the desired immune response to the antigen in question. To achieve this goal, the encapsulates can be surface-modified to have molecules that elicit phagocytic uptake by monocytes and macrophages. For example, molecules that have adjuvant activity can be used. Beta 1→4/1→6 glucan, zymosan, aluminum hydroxide, and other adjuvants known to those skilled in the art, may be utilized. For treating age-related macular degeneration (ARMD), the surface of the encapsulates in the formulation contain beta glucan, not just on the surface, but also in the interior of the encapsulates as an active, or as co-active with another drug. In another example, β-amyloid can bind beta glucan, thus acting as a homing signal for the encapsulates to bind to β-amyloid. In another embodiment, the molecules being released from each distinct matrix may be a combination of a therapeutic and an adjuvant.

In another embodiment, the surface characteristics of the encapsulates can be positively charged to adhere easily to the tissue surface, or to enhance permeation into cells. The surface of the encapsulates can be optimized to interact with the proteins in the tissue space.

The encapsulates are coated with polymers known to those skilled in the art to be compatible with and non-toxic to cells. In this connection, the encapsulates can be coated with polymers such as albumin, lecithin, phosphatidylcholine, PEG-distearoyl phosphatidyl choline (PEG2K/5K-DSPE), PEG-cholesterol, PEG, PEG-fatty acid (PEG-stearate, PEG-laureate, etc.) to prevent macro-encapsulation of the encapsulates as they release drug over a sustained period of time.

The drug contained within the matrices of the encapsulates may be hydrophilic, or hydrophobic. The drug can be a small molecule, a protein, a peptide, a peptide nucleic acid (PNA), oligonucleotide (ODN), DNA, an aptamer, or RNA. In one embodiment, the matrices can contain multiple small molecules, each with a distinct therapeutic intent.

In one embodiment, the injectable sustained-release formulation is injected into the conjunctival cul-de-sac of each eye to treat an ocular condition. The encapsulates in the injectable sustained-release formulation release at least 10 ng per day of a bioactive agent for a period greater than 2 weeks. In another example, the encapsulates release an effective amount of the one or more active agents for a period greater than 14 days in vivo, preferably greater than 60 days in vivo, more preferably up to 72 days in vivo, more preferably greater than 90 days in vivo, even more preferably over 100 days in vivo, and most preferably greater than 120 days in vivo.

In one embodiment, the encapsulates will be injected into ocular tissue to treat glaucoma. In one embodiment the drug is latanoprost, bimatoprost, travoprost, or their salts, esters, and prodrugs.

In another embodiment, the molecules being released from each distinct matrix may be a combination of a therapeutic and a p-glycoprotein (PGP) inhibitor.

In another embodiment, the molecules being released are a small molecule and a biologic, e.g., an anti-VEGF molecule to treat ARMD) and a steroid to treat inflammation. In an exemplary embodiment, the steroid is triamcinolone acetonide and the anti-VEGF molecule is avastin. In another example, the steroid is fluocinolone and the anti-VEGF molecule is PEGaptanib. In a further example, the anti-VEGF molecule is ranibizumab, bevacizumab, or aflibercept.

In another embodiment, the molecules being released from the matrices are an antimicrobial and a steroid. In another example, the anti-cancer molecule is an EGFR inhibitor. In one such example, the EGFR inhibitor is Ertolinib. In an example, the steroid is triamcinolone acetonide and the antimicrobial is tobramycin. Other antimicrobials that can be used are cortisporin, erythromycin, cyclosporin, and others in this class known to those skilled in the art.

Examples of corticosteroids and NSAIDs that can be incorporated into one of the matrices include, but are not limited to, dexamethasone, dexamethasone sodium phosphate, fluticasone propionate, fluticasone furoate, and diflu-prednate. In one example, one of the drugs is an antihistamine. In another example, one of the drugs is an anti-allergy medication.

In one embodiment, the drug-encapsulates are delivered as an intranasal wash, or an intranasal spray. In one example, the drug-encapsulates deliver an anti-allergy medication and a decongestant to the nasal passage. In another example, the intranasally-delivered matrix co-delivers an anti-allergy drug and an anti-inflammatory drug. In another example, the drug-encapsulates are administered to the lung as a spray-dried powder formulated with excipients made suitable for pulmonary administration. In another example, the drug-encapsulates are nebulized for pulmonary administration.

In another embodiment, one of the encapsulate layers contains a targeting moiety such as an antibody or a molecule targeting the encapsulates to a specific receptor. In this case, a second layer would contain a therapeutic to treat the disease.

In another embodiment, one of the layers may contain a biocompatible bioadhesive that can hold the delivery system to the tissue, while the layer contains a therapeutic, either a small molecule or a biologic. In an example, the bioadhesive molecule is polyacrylic acid and the therapeutic is a steroid.

In another embodiment, one of the layers may contain a cell-permeating component, while the other layer contained the therapeutic. In an example, the cell-permeating component is polysorbate 20, polysorbate 60, or polysorbate 80. In another example, the cell-permeating component is magainin, melittin, or any cell-permeating peptide known to those skilled in the art.

Also provided is a method for treating inflammation after cataract surgery. The method requires injecting the sustained-release formulation having loteprednol-containing microencapsulates into the conjunctival space after cataract surgery. The micro-encapsulates will release loteprednol etabonate over a period of three weeks at a sustained rate of 1-5 µg/day.

One aspect to successful drug therapy is the ability to treat the patient with multiple drugs, often with various drug release regimens. This results in the patient having to receive multiple drugs, often multiple injections, or multiple pills.

Oncology treatments often involve a combined drug regimen where multi-drug cocktails are utilized to develop an effective therapy for the patient. One example of a combined regimen is in the treatment of retinoblastoma, where the drug regimen could be sustained release of two different anti-cancer drugs. Another example of a combined drug regimen could be in the release of two different drugs, for the treatment of glioblastoma. In this example, the combined drug regimen could be precise and controlled release of a steroid and an anti-cancer drug. In another example, the combined drug regimen could be precise and controlled release of an anti-microbial and an anti-cancer drug.

In one example, the drug-containing encapsulates are small enough in dimensions to be sterile-filtered. The drug-containing encapsulates can be less than 0.22 microns in size, between 0.2-0.5 microns in size, 0.5-1 microns in size, 1-2 microns in size, 2-10 microns in size, 10-20 microns in size, 20-40 microns in size, 40-60 microns in size, 60-100 microns in size, 100-200 microns in size, or 200-500 microns in size.

The encapsulated drug in any given matrix may be released 100% in less than a day, or release in a sustained manner up to 14 days, or release in a sustained rate up to 14-30 days, or release in a sustained manner up to 30-150 days, or release in a sustained manner up to 150-180 days, or up to one year.

The therapeutic agents utilized with the drug-containing encapsulates can include one or more drugs set forth below, either alone or in combination. The drugs utilized may also be the equivalent of, derivatives of, or analogs of one or more of the drugs listed below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components.

Another example of a combined regimen would be in the treatment of macular edema caused by diabetic retinopathy (DR), or ARMD, among other posterior eye diseases. Since the macular edema is caused by inflammatory factors, it is often necessary to prescribe steroids or anti-inflammatory medications, also delivered by injections. The injectable sustained drug delivery system, which can release sustained, constant rates of multiple drugs simultaneously, could significantly alter the landscape of therapies available for these ocular diseases. Similarly, front-of-the-eye diseases can be treated by a single injectable sustained release drug delivery formulation that could release sustained, constant rates of multiple drugs.

Another example of a drug combination regimen that can be accomplished using the injectable sustained-release formulation described above is sustained release of an antibiotic and an anti-inflammatory after surgery. Examples of anti-inflammatories and analgesics used after cataract surgery are bromfenac, nevanac, durezol, fluticasone propionate, fluticasone furoate, dexamethasone, triamcinolone acetonide, ketorolac Tromethamine, flurbiprofen, morphine, and codeine.

One embodiment of a two drug-combination regimen is sustained release of an anti-microbial agent and an anti-inflammatory for the treatment of dermis-related diseases. In one example, the anti-microbial is an anti-fungal molecule. One embodiment of combined drug treatment could be in the treatment of urological diseases, with a concomitant administration of an antimicrobial and an anti-inflammatory. In another embodiment, the combined regimen is the administration of an imaging agent and a therapeutic.

In other embodiments, the injectable sustained-release formulation can be used for treating dermal disorders, CNS disorders, GI disorders, Alzheimer's disease or other disease of the brain, cardiovascular diseases, rectal diseases, and vaginal diseases.

In another embodiment, the injectable sustained-release formulation can be used for diagnostics. In another embodiment, the injectable sustained-release formulation can be used to deliver cosmetics or substances to improve appearance of the skin. In another example, the injectable sustained-release formulation can be utilized to deliver a therapeutic and a cosmetic.

The injectable sustained-release formulation can be incorporated into wound dressings.

Without further elaboration, it is believed that one skilled in the art can, based on the description above, utilize the present invention to its fullest extent. The specific examples below are to be construed as merely illustrative, and not limitative of the remainder of the disclosure in any way whatsoever.

EXAMPLES

Example 1

Fabrication and Characterization of Nanomesh Wafer Containing Travoprost

Fabrication

In this example, drug-loaded nanomesh wafers were prepared by electrospinning. This process makes use of electrostatic and mechanical force to spin fibers from the tip of a fine spinneret (See FIG. 1B). The spinneret is maintained at positive or negative charge by a DC power supply. When the electrostatic repelling force overcomes the surface tension force of the polymer solution, the liquid spills out of the spinneret and forms an extremely fine continuous filament. The dry mesh thus produced is porous and flexible, allowing it to be cut to a desired size. Raw materials were travoprost (Cayman Chemicals), PLGA RG503H (Evonik), PEG40-Stearate (Sigma-Aldrich), PEG3.35K (Carbowax), F127 (Spectrum), and PVP (Plastone, ISP).

Factors that control mesh properties are process conditions, molecular weight, conductivity of the solution, pH of the solution, distance from the tip to the collector and viscosity of the solution. Percent swelling of the mesh is controlled by the composition of the mesh; a mesh with high water-soluble content had higher hydration. For the purpose of an ocular insert, rapid hydration of the mesh causes formation of a tissue-compatible matrix.

TABLE 1

Solutions to prepare Nanomesh Wafer with Travoprost

Composition of Solution in the Syringe Prior to Electrospinning
% (w/w) in solution

| Lot No. | Travoprost | PEG3.33K | F127 | PEG40-Stearate | RG503H | Ethyl acetate | Ethanol | DMSO |
|---|---|---|---|---|---|---|---|---|
| ML-ES-06-5 | 3.00 | 0 | 0 | 3.15 | 26.87 | 61.77 | 7.27 | / |
| ML-ES-06-7 | 3.04 | 0 | 0 | 6.95 | 27.13 | 61.03 | 3.82 | / |
| ML-ES-06-8 | 3.04 | 0 | 3.13 | 0 | 27.05 | 61.65 | 0.07 | / |
| ML-ES-06-11 | 2.96 | 0 | 6.95 | 0 | 27.38 | 60.97 | 0.04 | / |
| ML-ES-06-12 | 2.99 | 3.16 | 0 | 0 | 26.93 | 61.47 | 0.07 | / |
| ML-ES-06-16 | 3.02 | 3.04 | 0 | 0 | 27.16 | 61.30 | 27.43 | 0.05 |
| ML-ES-06-21 | 2.97 | 0 | 0.75 | 0.75 | 27.17 | 61.78 | 8.67 | / |
| ML-ES-06-31 | 2.93 | 0 | 1.50 | 0.77 | 27.6 | 62.10 | 7.14 | / |

TABLE 2

Theoretical Composition of Ingredients in Nanomesh Wafer

| Lot No. | Visual | Travoprost | PEG3.33K | F127 | PVP | PEG40-Stearate | RG503H |
|---|---|---|---|---|---|---|---|
| ML-ES-06-5 | Flexible uniform | 3.00 | 0 | 0 | 0 | 10.17 | 86.78 |
| ML-ES-06-7 | Flexible uniform | 3.04 | 0 | 0 | 0 | 19.78 | 77.19 |
| ML-ES-06-8 | Flexible uniform | 3.04 | 0 | 10.06 | 0 | 0 | 86.90 |
| ML-ES-06-11 | Flexible uniform | 2.96 | 0 | 19.64 | 0 | 0 | 77.40 |
| ML-ES-06-12 | Flexible uniform | 2.99 | 10.20 | 0 | 0 | 0 | 86.81 |
| ML-ES-06-16 | Flexible uniform | 3.02 | 0 | 0 | 9.76 | 0 | 87.21 |
| ML-ES-06-21 | Flexible uniform | 2.97 | 0 | 2.54 | 0 | 2.54 | 91.95 |
| ML-ES-06-31 | Flexible uniform | 2.93 | 0 | 4.91 | 0 | 2.49 | 89.69 |

TABLE 3

Nanofiber Electrospinning Conditions

| Lot No. | Flow Rate (mL/hour) | Voltage (kV) | Needle (gauge) | Distance from Tip to Collector (inches) | Cycle |
|---|---|---|---|---|---|
| ML-ES-06-5 | 0.8 | 20 | 22 | 3.25 | 15 |
| ML-ES-06-7 | 0.8 | 20 | 22 | 3.25 | 15 |
| ML-ES-06-8 | 1.5 | 22 | 22 | 3.25 | 15 |
| ML-ES-06-11 | 1.5 | 22 | 22 | 3.25 | 15 |
| ML-ES-06-12 | 1.5 | 22 | 22 | 3.25 | 15 |
| ML-ES-06-16 | 2 | 16 | 22 | 3.25 | 15 |
| ML-ES-06-21 | 2 | 16 | 22 | 3.25 | 15 |
| ML-ES-06-31 | 2 | 16 | 22 | 3.25 | 15 |

The estimated travoprost content is 0.1575 mg for a prototype that is 10 mm×1.5 mm×0.22 mm (length×width×thickness). In a 30 day release profile, this would provide approximately 5.25 µg/day released on the ocular surface for absorption. It is estimated that 1.5 µg/day is needed for effective glaucoma therapy.

The thickness of the nanomesh was measured by a micrometer screw gauge (n=3). The results are shown in Table 4 below.

TABLE 4

Thickness of Nanomesh Wafer Prototypes

| sample | n = 1$^a$ | n = 2$^a$ | n = 3$^a$ | AVERAGE$^a$ | STDEV | RSD |
|---|---|---|---|---|---|---|
| ML-06-5 | 0.07 | 0.07 | 0.07 | 0.07 | 0.000 | 0.00% |
| ML-06-7 | 0.06 | 0.06 | 0.05 | 0.06 | 0.006 | 10.19% |
| ML-06-8 | 0.09 | 0.08 | 0.08 | 0.08 | 0.006 | 6.93% |
| ML-06-11 | 0.08 | 0.09 | 0.09 | 0.09 | 0.006 | 6.66% |
| ML-06-12 | 0.06 | 0.06 | 0.06 | 0.06 | 0.000 | 0.00% |
| ML-06-16 | 0.08 | 0.09 | 0.08 | 0.08 | 0.006 | 6.93% |
| ML-06-21 | 0.10 | 0.10 | 0.11 | 0.10 | 0.006 | 5.59% |
| ML-06-31 | 0.08 | 0.08 | 0.08 | 0.08 | 0.000 | 0.00% |
| ML-06-74 | 0.16 | 0.15 | 0.14 | 0.15 | 0.010 | 6.67% |
| ML-06-77 | 0.13 | 0.15 | 0.16 | 0.15 | 0.015 | 10.41% |
| ML-06-81 | 0.20 | 0.22 | 0.23 | 0.22 | 0.015 | 7.05% |
| ML-06-84 | 0.17 | 0.16 | 0.17 | 0.17 | 0.006 | 3.46% |
| ML-06-88 | 0.31 | 0.30 | 0.28 | 0.30 | 0.015 | 5.15% |

TABLE 4-continued

Thickness of Nanomesh Wafer Prototypes

| sample | n = 1$^a$ | n = 2$^a$ | n = 3$^a$ | AVERAGE$^a$ | STDEV | RSD |
|---|---|---|---|---|---|---|
| ML-07-07 | 0.07 | 0.07 | 0.09 | 0.08 | 0.012 | 15.06% |
| ML-07-08 | 0.48 | 0.44 | 0.45 | 0.46 | 0.021 | 4.56% |

$^a$values are thickness in mm

Encapsulation

To determine the percent drug encapsulation, travoprost encapsulated in nanomesh was dissolved first in acetonitrile. The polymer is precipitated in an aqueous phase and the supernatant analyzed by HPLC. Encapsulation is calculated by the following formula:

$$\text{Travoprost encapsulation (mg/g)} = \frac{\text{Travoprost}\left(\frac{\text{mg Travoprost}}{\text{g extraction solution}}\right) \times \text{Total mass of extraction solution (g)}}{\text{Mass of nanomesh (g)}}$$

The amount of travoprost in samples was determined by HPLC. For this analysis, a stock solution was prepared gravimetrically by weighing out 9.5 mg of travoprost and dissolving it in 0.9416 g methanol in a 1.5 mL centrifuge tube. This yielded a 9.9884 mg/g travoprost stock solution. Standards were prepared with concentrations between 0.007 and 142 µg/g, series diluted from the original 9.9884 mg/g travoprost stock solution. Standards prepared had a range of 0.00692 and 14.79 µg/mL. Analysis was conducted using a gradient program and Zorbax RP C-18 4.6×150 mm column, with a flow rate of 1 mL/min, 37° C., 220 nm, 20 minutes, 40 µL. Travoprost has a retention time of 19 minutes.

As shown below in TABLE 5 below, the percent encapsulation of the prototypes varied between 79-85%.

TABLE 5

Travoprost Encapsulation in Nanomesh

| Lot# | Encapsulation (mg travoprost/g mesh) | % Encapsulation |
|---|---|---|
| ML-ES-06-5 | 25.07 | 82.20 |
| ML-ES-06-7 | 25.84 | 85.28 |

TABLE 5-continued

Travoprost Encapsulation in Nanomesh

| Lot# | Encapsulation (mg travoprost/g mesh) | % Encapsulation |
|---|---|---|
| ML-ES-06-8 | 24.14 | 79.41 |
| ML-ES-06-11 | 25.43 | 85.62 |
| ML-ES-06-12 | 27.00 | 90.30 |
| ML-ES-06-16 | 24.96 | 82.65 |
| ML-ES-06-21 | 26.16 | 88.08 |
| ML-ES-06-31 | 25.73 | 87.82 |

Hydration

The rate of water absorption by nanomesh wafers was measured as a function of time. The hydration was performed using dry wafers incubated in buffer at 37° C. The results, shown in Table 6 below, indicated that the percent hydration was high when the hydrophilic component of the wafer was high. For wafers that had high hydrophobic content (e.g., ML-ES-06-7), hydration was relatively lower. In-vivo studies can be used to demonstrate if fast hydration kinetics results in delamination of the wafer from the ocular tissue.

TABLE 6

Hydration Kinetics of Nanowafer Prototypes

| Batch# | Final Composition in Dried Nanomesh Wafer | T = 10 m | T = 20 m | T = 30 m | T = 40 m | Appearance after hydration |
|---|---|---|---|---|---|---|
| ML-ES-06-5 | 10.17% PEG40-Stearate/3% TP/ | 149.32 | 146.58 | 154.79 | 154.79 | Intact, flexible |
| ML-ES-06-7 | 19.78% PEG Stearate/ | 44.90 | 75.51 | 32.65 | 51.02 | Intact, flexible |
| ML-ES-06-8 | 10% Pluronic F127 | 147.06 | 155.88 | 151.96 | 148.04 | Intact, flexible |
| ML-ES-06-11 | 20% Pluronic F127 | 56.38 | 57.45 | 59.57 | 56.38 | Intact, flexible |
| ML-ES-06-12 | 10% PEG3.35k | 76.62 | 90.91 | 94.16 | 90.91 | Intact, flexible |
| ML-ES-06-16 | 10% PVP | 43.71 | 55.09 | 53.89 | 55.09 | Intact, flexible |
| ML-ES-06-21 | 2.5% PEG-S & 2.5% F127 | 192.23 | 195.15 | 200 | 185.44 | Intact, flexible |
| ML-ES-06-31 | 2.5% PEG-S & 5% F127 | 251.16 | 258.14 | 265.12 | 267.44 | Intact, flexible |

Scanning Electron Microscopy

Scanning electron micrographs (SEMs) of prototypes showed a finely divided mesh nanostructure, with an open-celled structure with individual fibers between 200 nm and 5 microns in diameter. See FIG. 1C. The open cell structure allows free flow of fluids through the nanomesh wafer, a critical feature for a biocompatible insert.

In-Vitro Release

In-vitro release experiments with nanomesh wafers were conducted with 100 mg of wafer placed in Float-y-lyzer and incubated in buffer solutions at pH 7.4 and 37° C. The buffer contained 1% hydroxypropyl β-cyclodextrin (HPCD) in phosphate buffered saline (PBS). As shown in FIGS. 2A to 2D, in-vitro release of travoprost could be modulated by changes in the nanomesh composition.

Biodegradation and Potential for Local Irritation:

The potential risk for irritation in an ocular product is always a concern. To address this, an in-vitro study was conducted to ascertain the surface pH of the drug delivery system as it biodegraded and released drug into the buffer medium. A sensitive pH micro-probe was utilized to measure the surface pH of the system, on a nanomesh wafer prototype (ML-ES-06-31). The surface pH of the drug delivery system never fell dramatically; the pH fluctuated in the range of 6.9 to 7.2 for the duration of the study. See FIG. 3B. It is anticipated that the fluid turnover in an in-vivo scenario will wash out the low molar levels of lactic acid and/or glycolic acid released from the nanomesh wafer as it biodegrades.

Photo-Oxidation Stress:

Nanomesh wafers (ML-ES-06-31) were tested for photo-oxidative degradation by high intensity UV light (254 nm, for 24 hours). The data demonstrated that >98% of the encapsulated travoprost was intact, indicating protection of the drug from UV light exposure during use. In contrast, 50% of the travoprost in buffer alone was degraded under these conditions.

Figure 3A:
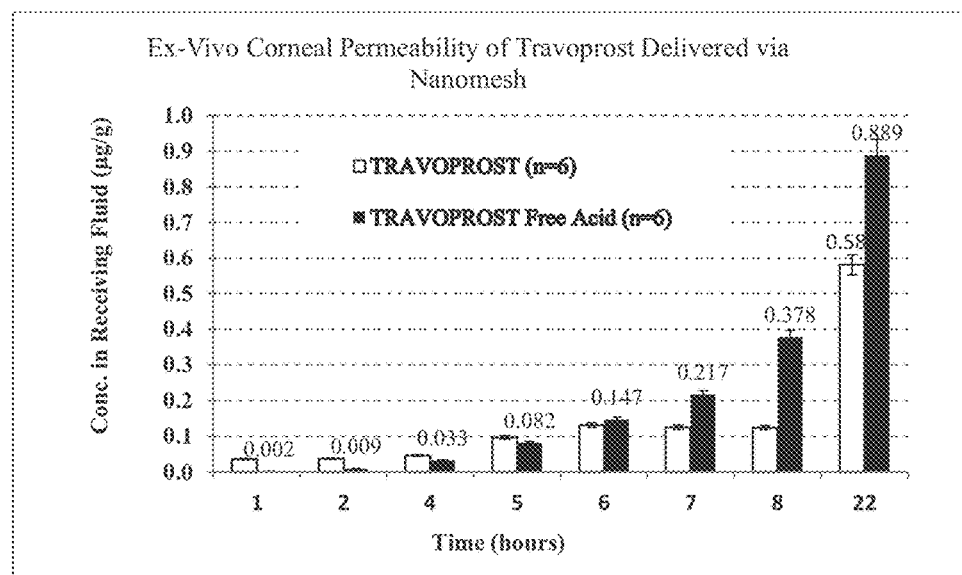
FIG. 3A is a bar graph showing the ex-vivo corneal permeability of travoprost released from a nanostructured biocompatible wafer over time.
Figure 3B:
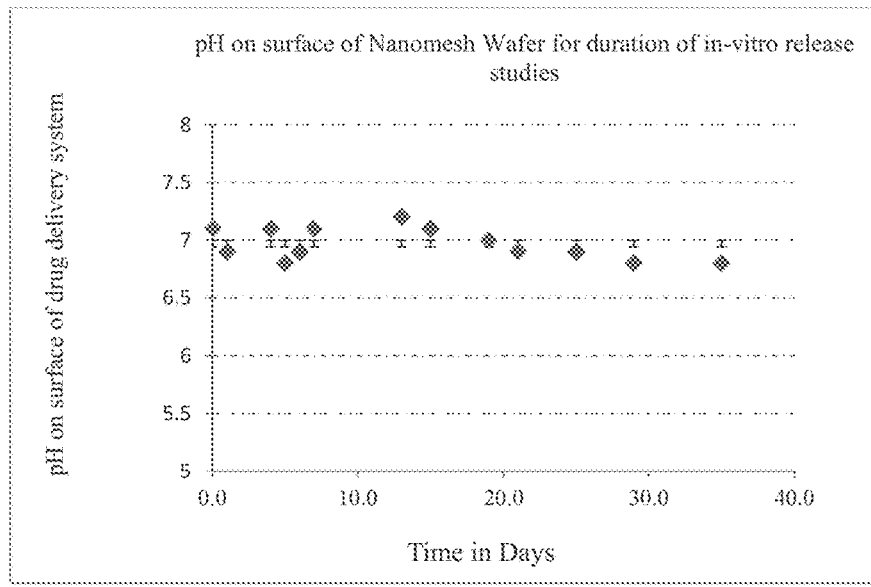
FIG. 3B is a graph showing the surface pH of the nanostructured biocompatible wafer over time during a drug release study.
Figure 3C:
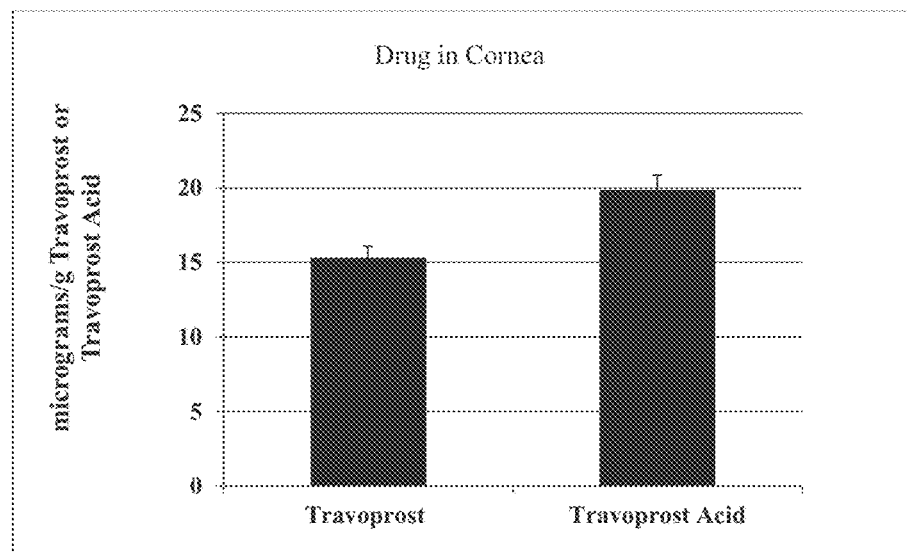
FIG. 3C is a bar graph showing the amount of travoprost and travoprost acid in the cornea following an ex-vivo corneal permeability assay.

Corneal Permeability Study:

Franz-cell corneal permeability studies were performed on Travoprost-containing nanomesh wafers (ML-ES-06-31). Fresh bovine calf corneas were loaded on the Franz diffusion cells. Nanomesh samples were punch-cut to have diameters of 5.28 mm and placed on the corneas. The samples were wet with 20 μL of buffer. The receptor chambers was filled with fresh 1% HPCD buffer. Time-points were once hourly for 8 hours and once after 18 hours. Samples were analyzed using a reverse-phase HPLC method. The corneas were retrieved from the chambers and extracted for drug content. FIG. 3A demonstrates that the encapsulated travoprost successfully diffuses through the bovine cornea to be converted into travoprost acid, the active form of the drug.

Example 2

Biocompatibility Screening of Prototypes

In-vitro eye irritation testing of three nanomesh wafer prototypes were tested for eye irritation using three-dimensional corneal tissue constructs purchased from Mattek Corporation, MA. Three nanomesh wafer prototypes were contact-exposed to the corneal tissue constructs using a published protocol. See Kandarova et al., Toxicology Letters 211, Supplement, 17 Jun. 2012, pages S111-S112, the content of which is incorporated herein in its entirety.

More than 60% cell viability is classified as "NI" (non-irritating). It was observed that the maximum thickness of a wafer should be no more than 0.5 mm to be non-irritating.

Example 3

Ocular Irritation in Rabbit Eyes

In vivo studies with the nanomesh wafers are conducted in normotensive New England White rabbits at Toxikon Corp, Bedford, Mass. Sterile meshes are inserted (blank nanomesh in one eye, travoprost-nanomesh in the opposite eye, n=6 rabbits) into the conjunctival cul-de-sac of each eye of the rabbit. Each eye is examined according to the McDonald-Shattuck Classification Grading Ocular Lesions prior to, and at specific time-points after placement of a travoprost-containing nanomesh wafer in one eye and a blank nanomesh wafer in the opposite eye. The following parameters are evaluated: Slit-lamp exam to include signs of ocular surface irritation (conjunctival hyperemia, chemosis, discharge, corneal opacity and fluorescein staining), inflammation (anterior chamber cells and flare, iritis), pupil diameter (calipers), and IOP (TonoVet rebound tonometer). Tear samples are collected using Schirmer strips for bioanalysis of travoprost and travoprost acid. On day 1, evaluations are conducted at baseline, 0.25, 0.5, 1, 2, 4, and 8 hours after nanomesh placement, followed by twice daily evaluations on days 2 and 3, then weekly for a total of 4 weeks. If at any point, severe irritation or inflammation is observed, e.g., persistent redness, discharge, chemosis, corneal staining, or cells and flare Grade 2 or higher, the nanomesh is removed and the animal will be allowed to recover. Minimal or no irritation is observed during the study duration for all nanomesh groups.

Example 4

Correlation of Biocompatibility with Modulus

Nanomesh prototypes are optimized to match the hydrated flexural modulus of the ocular conjunctiva. The optimal moduli range for a nanomesh wafer is ideally <25 MPa to be biocompatible.

Example 5

Correlation of Oxygen Permeability with Biocompatibility

Oxygen permeability correlates with irritation in ocular tissues. The optimal oxygen permeability range for nanomesh wafers is in the range of 20-30 Dk.

Example 6

Fabrication and Characterization of Nanomesh with Loteprednol Etabonate

TABLE 7

Solution Preparation for Loteprednol Etabonate Nanomesh

| | Composition | | | | |
|---|---|---|---|---|---|
| | % in mesh | | % in solution | | |
| Lot No. | API | 20 | RG503H | Ethyl acetate | Ethanol |
| ML-ES-03-48 | 6.53 | 0.74 | 26.56 | 59.56 | 11.19 |
| ML-ES-03-50 | 10.15 | 0.71 | 26.74 | 59.20 | 10.25 |

TABLE 8

Loteprednol Etabonate in Nanofiber Electrospinning Conditions

| Lot No. | Flow Rate (mL/hour) | Voltage (kV) | Needle (gauge) | Distance of Tip to Collector (inch) | Cycle |
|---|---|---|---|---|---|
| ML-ES-03-48 | 0.8 | 20 | 22 | 3.25 | 20 |
| ML-ES-03-50 | 0.8 | 20 | 22 | 3.25 | 15 |

TABLE 9

Characterization of Loteprednol Etabonate in Nanomesh

| Lot No. | Encapsulation (mg/g) | Burst (%) | % Release (40 Days) | % Hydration | Thickness (mm) | Flex Strength[a] | Visual Uniformity[b] |
|---|---|---|---|---|---|---|---|
| ML-ES-03-48 | 61.77 | 0 | 99.08 | 80.0 | 0.15 | 1 | 1 |
| ML-ES-03-50 | 96.27 | 0 | 55.09 | 89.3 | 0.10 | 1 | 1 |

[a]Flex Strength classify as Excellent (1), Good (2), Needs Improvement (3), Crumbles (4);
[b]Visual Uniformity classify as Excellent (1), Non-uniform in places (2) and Random/Non-uniform (3).

Thickness for these two nanomesh wafers were measured three times on three random areas. The standard deviation below 0.01 revealed the uniformity of loteprednol etabonate nanomesh wafers.

The total amount of encapsulated travoprost in each nanomesh wafer was measured by HPLC. The encapsulation for ML-ES-03-48 was 61.77 mg/g which was close to the target 6% in the mesh, and the encapsulation for ML-ES-03-50 was 96.27 mg/g which was also close to the target 10% in the mesh.

None of these nanomesh prototypes released drug in 1 hour. For in vitro release, ML-ES-03-48 released 99.08% in 40 days, which was close to a desired target of releasing 100% in 30 days, while the cumulative release of ML-ES-03-50 in 40 days was comparatively slow, which may have resulted from lower PEG.S than ML-ES-03-48. The flexural strength of these two nanomesh wafer prototypes was excellent. They can both be bent and flexed between thumb and index finger. It was observed that ML-ES-03-48 and ML-ES-03-50 were made uniformly.

Example 7

Fabrication of Nanomesh with Surface Reactive Moieties

Nanomesh wafers can be prepared by incorporating 5% 4-arm PEG3K-succinimidyl glutarate (SG) and 4-arm 5% PEG-NH$_2$ with 26% PLGA (RG503H), 0.7% PEG-Stearate in the electrospinning solution in the same solvents shown in Table 7 above, with 49% ethyl acetate and 11% ethanol and the active pharmaceutical ingredient (API), in this case, loteprednol etabonate. The conditions of the electrospinning are shown in Table 8 above.

Example 8

Fabrication and Characterization of Loteprednol Etabonate in PLG Microencapsulates Loteprednol etabonate is a "soft" steroid which is rapidly converted into inactive metabolites by nonspecific esterases in the ocular tissue. A micro-encapsulated loteprednol etabonate injectable sustained-release formulation is disclosed that can be injected in the conjunctival sac immediately after surgery. For control of inflammation after cataract surgery, the injectable sustained-release formulation is designed to release a drug over a 2 to 3 week period with a single injection.

PLG was used as the biodegradable polymer microencapsulate. The roles of molecular weight, structure, and size of the microencapsulates on the release profile of loteprednol etabonate were investigated, as well as injectability as a function of size.

Preparation of Micro-encapsulates:

PLG microencapsulates were prepared by an emulsion process to achieve a narrow size distribution, optimum size, and injectability. Loteprednol etabonate was purchased from Sigma, Inc. PLG (50:50 L:G) of different molecular weights were utilized to assess effect on in-vitro release. A blend of PLG terminated with acid end groups and ester end groups were prepared to assess the effect on in-vitro drug release. The microencapsulates were prepared as follows:

a. A stock solution of 8% polyvinyl alcohol (PVA) was prepared by adding solid PVA to distilled water while stirring, and then heating to 80° C. When fully dissolved, the solution was allowed to cool back down to 25° C., and then 53 g of the solution was aliquoted for Phase II preparation. A 9.46% sodium chloride solution was prepared separately from the 8% PVA. The sodium chloride was poured into the PVA solution slowly, while the PVA solution was stirring. 3.6 grams of ethyl acetate was added to the Phase II. The Phase II was then covered and refrigerated at 4° C. Prior to homogenization, the Phase II was poured into a jacketed vessel when it had reached 0° C.

b. A 50/50 v/v mixture of ethanol and ethyl acetate was prepared. The weights were obtained and recorded. Loteprednol etabonate was dissolved in this mixture to create a 30 mg/mL solution of loteprednol etabonate. In exemplary formulation KB-ES-02-55, the loteprednol solution also contained 5% w/w PE/F-127.

c. PLG was dissolved in ethyl acetate to create a 5.2% solution. 1 mL of the loteprednol etabonate stock solution was aliquoted into the PLG solution while it stirred. The completed Phase I was taken up into a Hamilton #1010 Gastight syringe fitted with 14 ga tubing. The Phase I was used immediately after preparation. It should not be left at room temperature, nor should it be refrigerated. The homogenization run was started, and the Phase I was injected into the Phase II to generate an emulsion, i.e., Phase III. Immediately afterward, the Phase III was poured into additional H$_2$O to create the final microsphere suspension.

d. After 6 minutes of homogenization, the jacketed vessel was moved to a paddle mixer and stirred for 3 h at 450 RPM. During this step, the first hour of stirring was conducted at 0° C. Then, the temperature was raised to 17° C. for 20 min., then 27° C. for 20 min., and then 35° C. for the remaining time. After 3 h elapsed, the suspension was cooled to 10° C. and pipetted into 50 mL centrifuge tubes. The samples were centrifuged 3 times at 10000 RPM, 10° C.

e. The first centrifugation cycle results in a pellet of microspheres and a supernatant composed of the bulk of the PVA, NaCl, and remaining ethyl acetate.

f. The microencapsulates were washed four times with 4° C. distilled water and the pellets combined into one. The microencapsulates were sprayed with dimethicone in isopropanol to provide a non-aggregating surface.

g. The combined pellet was re-suspended and washed with 5-10 mL of chilled distilled water, in a 100 mL beaker. The beaker was covered with a lint-free paper and then placed in a lyophilizer for drying.

Characterization of Microencapsulates:
Particle Size Distribution (PSD):

Samples were suspended 20 mg/mL in a diluent, diluted with an equivalent volume of water. 500 µL of the suspension was dispersed in a dispersal medium (a thirty fold dilution of the diluent in distilled water). Particle size was measured on a Horiba LA-950 Laser Diffraction Particle Analyzer.

Imaging:

Dry encapsulates were characterized by scanning electron microscopy.

Encapsulation (mg/G):

20 mg of the microencapsulate was dissolved in 1 mL of acetonitrile, and 10 mL of isopropanol added drop-wise while mixing. 1 mL of the slurry was centrifuged (5 min.; 6000 RPM), and the supernatant was removed for HPLC analysis. HPLC analysis was performed on a RP C18 column.

Compatibility:

The compatibility of PLG and loteprednol etabonate was assessed by comparison of their HPLC profiles.

In-Vitro Burst (%):

30 mg of the microencapsulates were reconstituted in 1 mL of PBS, pH 7.4 and rotated at 37° C., in a 2 mL polypropylene centrifuge tube. At the 1 hour time-point, the centrifuge tubes were spun down at 15,000 RPM. One mL of the supernatant was removed for analysis by HPLC.

In-Vitro Release:

200-300 mg of microencapsulates were weighed into 1 mL SpectraPor cassettes (cellulose membranes, MWCO 1000 kDal). The cassettes containing the microencapsulates were placed in 45 mL of PBS and incubated at 50° C. Time point samples were obtained after 1 hour and daily over the course of 20 days. The samples were analyzed by HPLC.

Injectability:

Injectability of the microencapsulates suspended in the reconstituting fluid was tested both through 23 G and 27 G needles.

The results of the analysis are presented in Table 10 below. The data demonstrated that loteprednol etabonate could be encapsulated successfully in PLG-based microencapsulates. The size distribution of the microencapsulates can be modulated by control of process conditions, with a range of sizes between 9.3-40.4 microns ($d_{50}$). An accelerated in-vitro release test was developed to enable fast screening of prototypes to assess difference in in-vitro release of drug produced as a function of size, polymer structure and molecular weight. Through this test, it was ascertained that PLG of higher molecular weight and larger size (KB-05-01) released drug very slowly, as opposed to a blend prototype of ester end and acid end PLG (50:50 L:G) (KB-05-34). Surprisingly, the release rate of drug from ester end group PLG microencapsulates (KB-05-25B) was greater that that rate from acid end group PLG microencapsulates (KB-05-28) at the same MW (0.21 dl/g).

All batches were injectable through 27 G needles for the entire size range of the prototypes, which renders it feasible for injection in ocular tissue. PLG polymers and loteprednol etabonate were deemed compatible. All PLG microencapsulates were designed to have a solid microstructure.

TABLE 10

Characterization of Loteprednol Etabonate-Containing Microencapsulates

| Lo# | Polymer Name | Intrinsic Viscosity | Encap. | PSD ($d_{50}/d_{90}$) |
|---|---|---|---|---|
| KB-05-01 | Purasorb 5004A; 50/50 L:G | 0.39 dl/g | 187.9 mg/g | 40.4/67 |
| KB-05-25A | Purasorb 5002; 50/50 L:G | 0.2 dl/g | 19.8 mg/g | 15/41.9 |
| KB-05-25B | Purasorb 5002; 50/50 L:G | 0.2 dl/g | 29.4 mg/g | 16.7/37.2 |
| KB-05-28 | Purasorb 5002A; 50/50 L:G | 0.21 dl/g | 47.5 mg/g | 11.6/24.3 |
| KB-05-34 | Mix: A 50/50 combination of Purasorb 5002 and 5002A, both 50/50 L:G | 0.21 dl/g | 14.9 mg/g | 9.3/21 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present invention, and without departing from the spirit and scope thereof, can make various changes and modifications of the present invention to adapt it to various usages and conditions. Thus, other embodiments are also within the claims.

The invention claimed is:

1. A nanostructured biocompatible water tor drug delivery to a tissue, the wafer comprising a tissue-reactive mucoadhesive polymer and a mesh formed of a plurality of polymer fibers, wherein the tissue-reactive mucoadhesive polymer is coated on the wafer or intercalated with the fibers, the wafer has a hydrated flexural modulus less than 25 MPa, the mesh has a pore size of 50 nm to 1000 nm, and the polymer fibers have a diameter of 100 nm to 1500 nm.

2. The nanostructured biocompatible wafer of claim 1, wherein the polymer fibers are formed of the polymers selected from the group consisting of polylactide-co-glycolide, polylactic acid, polycaprolactone, poly(trimethylene carbonate), poly(amino acids), hyaluronic acid, polyethylene glycol (PEG), polyethylene oxide -polypropylene oxide - polyethylene oxide tri-block copolymer, PEG-stearate, PEG-distearoyl-sn-glycero-3-phosphoethanolamine, lecithin, xanthan, polyvinylalcohol, polyvinylpyrrolidone, albumin, collagen, polysiloxane, polymethylmethacrylate, and a combination thereof.

3. The nanostructured biocompatible wafer of claim 1, wherein the tissue-reactive mucoadhesive polymer is selected from the group consisting of xanthan gum, guar gum, chitosan, hyaluronic acid, alginate, xyloglucans, polycarbophil, polyacrylic acid, tamarind seed polysaccharide, PEG-succinimidyl glutarate, PEG-amine, polylysine, and a combination thereof.

4. The nanostructured biocompatible wafer of claim 1, wherein the polymer fibers are monolithic fibers and the tissue-reactive mucoadhesive polymer is intercalated with the polymer fibers.

5. The nanostructured biocompatible wafer of claim 4, further comprising a wound healing component selected from 1→3 beta glucan, 1→6 beta glucan, tamarind seed polysaccharide, albumin, lecithin, collagen, and hyaluronic acid.

6. The nanostructured biocompatible wafer of claim 4, further comprising succinimidyl, thiol, or amine moieties for binding to the tissue via ionic binding or light complexation to proteins on a surface of the tissue.

7. The nanostructured biocompatible wafer of claim 1, wherein the mesh is formed of a plurality of co-axial fibers each having a core containing the plurality of polymer fibers and an outer layer containing the tissue-reactive mucoadhesive polymer.

8. The nanostructured biocompatible wafer of claim 7, further comprising a wound healing component selected from 1→3 beta glucan, 1→6 beta glucan, tamarind seed polysaccharide, albumin, lecithin, collagen, and hyaluronic acid.

9. The nanostructured biocompatible wafer of claim 7, further comprising succinimidyl, thiol, or amine moieties for binding to the tissue via ionic binding or light complexation to proteins on a surface of the tissue.

10. The nanostructured biocompatible wafer of claim 1, wherein the wafer has an oxygen permeability of 15 Dk to 30 Dk.

11. The nanostructured biocompatible wafer of claim 1, wherein the wafer has a thickness of 0.05 mm to 0.5 mm.

12. The nanostructured biocompatible wafer of claim 1, further comprising a first drug contained within the polymer fibers.

13. The nanostructured biocompatible wafer of claim 12, wherein the first drug is a small molecule, a protein, a peptide, or a nucleic acid.

14. The nanostructured biocompatible wafer of claim 1, further comprising a first drug contained in microparticles deposited on the polymer fibers.

15. The nanostructured biocompatible wafer of claim 12, wherein the first drug is an anti-glaucoma agent, an anti-viral agent, an anti-inflammatory steroid, a non-steroidal anti-inflammatory, an anti-fungal agent, an anti-bacterial agent, an anti-allergy agent, an agent to treat dry eye, a wound healing agent, an agent to heal ocular injury, an analgesic, an anesthetic or an agent to treat rosacea.

16. The nanostructured biocompatible wafer of claim 12, further comprising a second drug different from the first drug, wherein the polymer fibers are co-axial fibers having an inner layer formed of a first polymer and an outer layer formed of a second polymer, the first drug being contained within the inner layer and the second drug being contained within the outer layer.

17. The nanostructured biocompatible wafer of claim 16, wherein the first polymer is different from the second polymer.

18. The nanostructured biocompatible wafer of claim 16, wherein the inner layer and the outer layer are formulated to release the first drug and the second drug at different rates.

19. A method for treating an ocular disease, the method comprising identifying a subject in need of treatment, obtaining the nanostructured biocompatible wafer of claim 15, placing the nanostructured biocompatible wafer onto a conjunctiva of the subject, and maintaining the nanostructured biocompatible wafer on the conjunctiva for 1-180 days.

20. A method for treating an ocular surface disorder, the method comprising identifying a subject in need of treatment, obtaining the nanostructured biocompatible wafer of claim 15, and placing the nanostructured biocompatible wafer onto a conjunctiva of the subject.

21. The method of claim 20, wherein the ocular surface disorder is dry eye, rosacea, allergic conjunctivitis, glaucoma, keratitis, blepharitis, corneal tear/injury, or inflammation.

22. A method for treating an ocular surface infection, the method comprising identifying a subject in need of treatment, obtaining the nanostructured biocompatible wafer of claim 15, placing the nano structured biocompatible wafer into a conjunctival cul-de-sac of the subject, and maintaining the nanostructured biocompatible wafer on the conjunctiva for a period of 2 weeks to 2 months.

23. An injectable sustained-release formulation for treating an ocular disorder, the formulation comprising a drug contained within a plurality of microparticles each formed of a biodegradable polymer, and a dispersant compound coated on the microparticles, the microparticles having a size of 1 µm to 40 µm, wherein the microparticles contain 20% to 30% by weight of the biodegradable polymer and 5% to 20% by weight of the dispersant compound and the dispersant compound is selected from the group consisting of a silicone, lecithin, phosphatidylcholine, albumin, collagen, a polyethylene glycol (PEG)-fatty acid, a polyurethane, PEG-lecithin, poly(propylene oxide)-poly(ethylene oxide)-poly(propylene oxide), glycocholic acid, and cholic acid.

24. The formulation of claim 23, wherein the PEG-fatty acid is PEG-stearate, PEG-laurate, or PEG40-stearate.

* * * * *